(12) United States Patent
Shi et al.

(10) Patent No.: US 11,597,725 B2
(45) Date of Patent: *Mar. 7, 2023

(54) URAT1 INHIBITOR FOR PROMOTING URIC ACID EXCRETION

(71) Applicant: JIANGSU ATOM BIOSCIENCE AND PHARMACEUTICAL CO., LTD., Zhenjiang (CN)

(72) Inventors: Dongfang Shi, Fremont, CA (US); Jianghua Zhu, Zhenjiang (CN); Jie Gu, Zhenjiang (CN); Xi Cheng, Zhenjiang (CN); Yan Yang, Zhenjiang (CN); He Zhou, Zhenjiang (CN); Pengfei Li, Zhenjiang (CN); Fan Wu, Zhenjiang (CN)

(73) Assignee: JIANGSU ATOM BIOSCIENCE AND PHARMACEUTICAL CO., LTD., Suzhou (CN)

( * ) Notice: Subject to any disclaimer, the term of this patent is extended or adjusted under 35 U.S.C. 154(b) by 41 days.

This patent is subject to a terminal disclaimer.

(21) Appl. No.: 16/617,426

(22) PCT Filed: May 25, 2018

(86) PCT No.: PCT/CN2018/088400
§ 371 (c)(1),
(2) Date: Nov. 26, 2019

(87) PCT Pub. No.: WO2018/214961
PCT Pub. Date: Nov. 29, 2018

(65) Prior Publication Data
US 2020/0262832 A1    Aug. 20, 2020

(30) Foreign Application Priority Data
May 26, 2017  (CN) .......................... 201710386922.4

(51) Int. Cl.
| | | |
|---|---|---|
| *C07D 471/04* | (2006.01) | |
| *A61P 19/06* | (2006.01) | |
| *C07D 231/56* | (2006.01) | |
| *C07D 487/04* | (2006.01) | |
| *C07D 491/052* | (2006.01) | |

(52) U.S. Cl.
CPC ............ *C07D 471/04* (2013.01); *A61P 19/06* (2018.01); *C07D 231/56* (2013.01); *C07D 487/04* (2013.01); *C07D 491/052* (2013.01)

(58) Field of Classification Search
CPC .. C07D 471/04; C07D 231/56; C07D 487/04; C07D 491/052; A61P 19/06
See application file for complete search history.

(56) References Cited

U.S. PATENT DOCUMENTS 10,875,865 B2 * 12/2020 Shi ..................... C07D 491/048

FOREIGN PATENT DOCUMENTS

| CN | 1064332229 | * | 2/2017 | ........... C07D 471/04 |
| WO | WO-2015086498 A1 | * | 6/2015 | .............. A61P 27/00 |

OTHER PUBLICATIONS

English Translation of CN 106432229 A (Atom Bioscience and Pharmaceutical Co LTD). Published on Feb. 22, 2017. Retrieved on Dec. 15, 2021 from http://www.ip.com. (Year: 2017).*
Tausche AK, Richter K, Grässier A, et alSevere gouty arthritis refractory to anti-inflammatory drugs: treatment with anti-tumour necrosis factor α as a new therapeutic optionAnnals of the Rheumatic Diseases 2004;63:1351-1352. (Year: 2004).*

* cited by examiner

*Primary Examiner* — Brandon J Fetterolf
*Assistant Examiner* — Lauren Wells
(74) *Attorney, Agent, or Firm* — CBM Patent Consulting, LLC

(57) ABSTRACT

The present invention belongs to the field of medicinal chemistry. Specifically disclosed is a class of URAT1 inhibitors for promoting uric acid excretion, which are compounds as represented by the structure of formula (I) or pharmaceutically acceptable salts thereof. Experiments show that the compounds provided by the present invention have a very good inhibitory effect on the transport of uric acid by hURAT1 in HEK293 transfected cells, and that such compounds have a good application prospect in the treatment of hyperuricemia or gout.

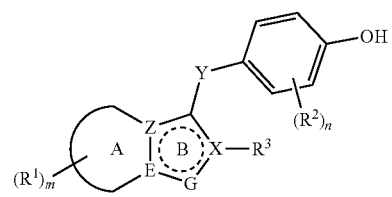

10 Claims, No Drawings

URAT1 INHIBITOR FOR PROMOTING URIC ACID EXCRETION

TECHNICAL FIELD

The invention belongs to the field of medicinal chemistry and particularly relates to a class of URAT1 inhibitor compounds for increasing uric acid excretion and applications in medicine.

BACKGROUND OF THE INVENTION

Gout is one of the most common types of arthritis caused by hyperuricemia. At present, there are nearly 100 million gout patients worldwide, and its market size is huge. According to statistics, the incidence of gout in Europe is about 1-2%, mostly in middle-aged men (Michael Doherty, Tim L Jansen, George Nuki, et al. Gout: why is this curable disease so seldom cured? Annals of the Rheumatic Diseases. 2012, 71(11): 1765-1770). The number of gout patients in the US has also reached 8.3 million (Zhu Y, Pandya B J, Choi H K. Prevalence of gout and hyperuricemia in the US general population: the National Health and Nutrition Examination Survey 2007-2008. Arthritis Rheumatol 2011, 63(10): 3136-3141). The number of hyperuricemia patients in China is about 120 million, of which more than 50 million are gout patients, and the number of male gout patients is much higher than that of women.

Usually, when the patients' serum uric acid is greater than 6.8 mg/dL, we call them hyperuricemia patients. When the uric acid concentration exceeds the maximum solvency in the serum, urate will form crystal deposits in the synovial fluid of tissues, the cartilage of the peripheral joints, the auricles of the ears, and the olecranon of the elbows (Richette P, Bardin T Gout. Lancet. 2010, 375 (9711): 318-328), causing repeated inflammatory arthritis, producing gout flares, and eventually leading to severe chronic joint disease and even bone erosion (Schlesinger N. Difficult-to-treat gouty arthritis: a disease warranting better management. Drugs, 2011, 71(11): 1413-1439). When urate crystals form and deposit in the subcutaneous tissue, tophi will form, which can rupture the human epidermal tissue, causing pain and even infection.

At present, the standardized treatment for gout includes a treatment for lowering the concentration of serum uric acid (urate-lowering therapy, ULT), which can lower the serum uric acid concentration below the saturation concentration without forming urate crystals, and can make the urate crystals dissolved at the lesions. Gout will no longer form after the disappearance of urate crystals in the body. The American College of Rheumatology (ACR) and the European League Against Rheumatism (EULAR) recommend that the serum uric acid concentration of patients with general gout should be treated to be less than 6 mg/dL, while the serum uric acid concentration of patients with tophi should be treated to be less than 5 mg/dL. Multiple studies have shown that continuous reduction of serum uric acid concentration can reduce the severity of clinical gout, the incidence of acute gout flares (Shoji A, Yamanaka H, Kamatani N. A retrospective study of the relationship between serum urate level and recurrent attacks of gouty arthritis: evidence for reduction of recurrent gouty arthritis with antihyperuricemic therapy. Arthritis Rheum. 2004, 51(3): 321-325), and the size and number of tophi (Perez-Ruiz F, Calabozo M, Pijoan J I, et al. Effect of uratelowering therapy on the velocity of size reduction of tophi in chronic gout. Arthritis Rheumatology, 2002, 47(4): 356-360).

ULT mainly includes decreasing uric acid production therapy (such as xanthine oxidase inhibitors) and increasing uric acid excretion therapy (such as URAT1 inhibitors) according to the mechanism of action. The more often used xanthine oxidase inhibitors mainly includes allopurinol and febuxostat, which are the first-line treatments for gout patients in Europe and the United States, but a large number of studies have shown that about 80-85% of hyperuricemia patients suffer the disease due to the inadequate excretion of uric acid by the kidneys. (Cheeseman C Solute carrier family 2, member 9 and uric acid homeostasis. Current Opinion in Nephrology and Hypertension, 2009, 18(5): 428-432). Therefore, the clinical treatment effect of xanthine oxidase inhibitor is not satisfactory, about 40-80% of patients fail to achieve the purpose of controlling serum uric acid level by the treatment of uric acid production inhibitors (Edwards N L. Febuxostat: a new treatment for hyperuricaemia in gout. Rheumatology (Oxford). 2009, 48(2): 15-19). Since allopurinol has a weak clinical efficacy (Rashid N, Coburn B W, Wu Y L, et al. Modifiable factors associated with allopurinol adherence and outcomes among patients with gout in an integrated healthcare system. Journal of Rheumatology. 2015, 42(3): 504-512), most patients who received a dose of 300 mg/day allopurinol still have a serum uric acid concentration above the target value, and fatal rash and a variety of adverse reactions may be caused; although 80 mg/day of febuxostat has a better efficacy than treatment of allopurinol 300 mg/day (Schumacher H R, Jr., Becker M A, Wortmann R L, et al. Effects of febuxostat versus allopurinol and placebo in reducing serum urate in subjects with hyperuricemia and gout: a 28-week, phase III, randomized, double-blind, parallel-group trial. Arthritis Rheumatology. 2008, 59(11): 1540-1548), there are still 40%-52% of patients whose serum uric acid concentration has not dropped to the target value, and febuxostat also has serious side effects of cardiovascular, gastrointestinal discomfort and liver toxicity. Therefore, the ACR guidelines for management of gout recommend the addition of a drug that promotes uric acid excretion (Khanna D, Fitzgerald J D, Khanna P P, et al. 2012 American College of Rheumatology guidelines for management of gout, part 1: systematic non-pharmacologic and pharmacologic therapeutic Approaches to hyperuricemia. Arthritis Care & Research. 2012, 64(10): 1431-1446).

Increasing uric acid excretion drugs plays an important role in the treatment of hyperuricemia and gout. The mechanism of action is to inhibit the reabsorption of uric acid in the proximal convoluted tubules of the kidney and increase the renal excretion of uric acid, thereby decreasing the concentration of serum uric acid. Human urate anion transporter 1 (hURAT1) is a member of the organic anion transporter (OAT) superfamily. It is encoded by the SLC22A12 gene, and its cDNA has many mutations that cause uric acid metabolism abnormally. hURAT1 protein, which is specifically expressed on the brush border membrane of epithelial cells of human renal proximal convoluted, is the most important uric acid reabsorption protein in human body and controls the reabsorption of more than 90% of uric acid after glomerular filtration (Michael F W, Jutabha P, Quada B. Developing potent human uric acid transporter 1 (hURAT1) inhibitors. Journal of Medicinal Chemistry. 2011, 54: 2701-2713). Inhibition of hURAT1 transport can effectively reduce uric acid reabsorption, promote uric acid excretion in the kidney, and decrease serum uric acid levels in the body (Michael F W, Jutabha P, Quada B. Developing potent human uric acid transporter 1 (hURAT1) inhibitors. Journal of Medicinal Chemistry. 2011, 54:2701-2713).

URAT1 inhibitors currently used for gout treatment include benzbromarone, Zurampic, probenecid and sulfinpyrazone. Benzobromarone is currently the most effective drug for increasing uric acid excretion on the market. However, benzbromarone has severe liver toxicity and has not been approved in the US market. And it has been withdrawn from most European countries in 2003 (Jansen T L, Reinders M K, van Roon E N, et al. Benzbromarone withdrawn from the European market: another Case of "absence of evidence is evidence of absence". Clinical Experimental Rheumatology, 2004, 22(5): 651). Another disadvantage is that it has a strong inhibitory effect on the liver CYP2C9 of P450s enzymes. However, due to the lack of good gout drugs on the market, it is still used in more than 20 countries including China, Germany, Japan, Brazil, and New Zealand. Probenecid and sulfinpyrazone have very low efficacy and severe side effects.

Lesinurad (RDEA-594), trade name as Zurampic, is a novel URAT1 inhibitor developed by Ardea Biosciences. AstraZeneca acquired the drug by spending S1.26 billion acquiring Ardea in 2012. Zurampic was approved in the United States and Europe in December 2015 and February 2016 at a dose of 200 mg/day in combination with allopurinol, which is much worse efficacy than benzbromarone (50-80 mg/day). A phase III clinical trial of Zurampic in combination with febuxostat in the treatment of gout showed after 12 months of uric acid control treatment by using a combination group of 200 mg Zurampic+80 mg febuxostat and placebo group (80 mg febuxostat alone), there was no significant difference in the percentage of patients with reaching serum uric acid sUA<5 mg/dl. Zurampic also has a variety of toxic side effects: (1) the drug may cause a major cardiovascular adverse event in patients with fatal cardiovascular disease, non-fatal myocardial infarction or cerebral palsy. (2) There is a renal function-related adverse reaction immediately after the start of treatment with Zurampic. When taking 400 mg Zurampic alone, there is the highest incidence of serious adverse events. Therefore, high-dose single-use of Zurampic is prohibited clinically, and renal function should be detected regularly before and after treatment. Therefore, the FDA requires to indicate its severe renal toxicity with a black box in its drug label. (3) The drug can cause mild to moderate liver damage. Although the FDA has approved the listing of Zurampic, the lack of significant efficacy and toxicity has made the product's prospect bleak.

SUMMARY OF INVENTION

The objective of the present invention is to provide a series of new compounds based on the current technologies, aiming to obtain a URAT1 inhibitor with low toxicity and good efficacy for the treatment of hyperuricemia or gout.

The objective of the invention can be achieved by the following measures:

Provided is a compound of Formula (I)

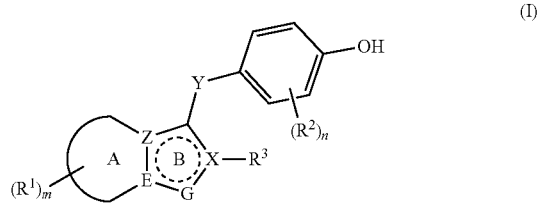

(I)

wherein,

A is a non-aromatic six-membered ring with or without a hetero atom O, N or S;

Ring B is a five-membered aromatic ring or a furan ring containing two N atoms;

Z, E or X are each independently C or N atom;

G is an N or O atom; and when G is an O atom, Z, E and X are all C atoms; when G is an N atom, only one of Z, E and X is an N atom;

Y is carbonyl, sulfur, sulfone, sulfoxide, optionally substituted methylene or imino;

$R^1$ is one or more selected from the group consisting of hydrogen, deuterium, hydroxy, halogen, nitro, amino, cyano, $C_{1-5}$ alkyl, substituted $C_{1-5}$ alkyl, substituted $C_{1-3}$ amino, $C_{1-3}$ alkoxy, substituted $C_{1-3}$ alkoxy and $C_{1-5}$ alkylthio;

$R^2$ is one or more selected from the group consisting of hydrogen, deuterium, hydroxy, halogen, nitro, amino, cyano, $C_{1-4}$ alkyl, substituted $C_{1-3}$ alkyl, $C_{2-3}$ alkenyl, $C_{2-3}$ alkynyl, substituted $C_{1-3}$ amino, $C_{1-5}$ alkoxy, substituted $C_{1-5}$ alkoxy and $C_{1-5}$ alkylthio;

$R^3$ is $C_{1-4}$ alkyl, substituted $C_{1-4}$ alkyl or $C_{3-4}$ cycloalkyl;

m is an integer from 0 to 3;

n is an integer from 1 to 3;

The substituent in the group Y is selected from the group consisting of hydroxyl, cyano, nitro, amino, carboxyl or $C_{1-3}$ alkoxy, the substituent in the group $R^1$, $R^2$ or $R^3$ is selected from the group consisting of hydroxyl, halogen, nitro, amino and cyano.

When m in the present invention is 2 or 3, it means that the compound contains two $R^1$ groups, and the two $R^1$ groups may be the same, and the groups defined by $R^1$ in the present application may also be used, respectively.

When n in the present invention is 2 or 3, it means that the compound contains two $R^2$ groups, and the two $R^2$ groups may be the same, and the groups defined by $R^2$ in the present application may also be used, respectively.

In one embodiment, Ring A is a cyclohexene ring or a non-aromatic six-membered ring containing at least one O or/and N atom.

In a preferred embodiment, Ring A is a cyclohexene ring, a 3,4-dihydro-2H-pyran ring, a tetrahydropyran ring, a 2,3,4,5-tetrahydropyridine ring, a 5,6-dihydro-2H-1,3-oxazine ring or a 1,2,5,6-tetrahydropyrimidine ring.

In one embodiment, $R^1$ is selected from one or more of the group consisting of hydrogen, deuterium, fluorine, chlorine, bromine, hydroxy, cyano, $C_{1-3}$ alkyl, $C_{1-3}$ haloalkyl and $C_{1-3}$ alkoxy; m is 0, 1 or 2.

In a preferred embodiment, $R^1$ is selected from one or more of the group consisting of hydrogen, deuterium, fluorine, chlorine, bromine, cyano, methyl, ethyl, methoxy, ethoxy; m is 0, 1 or 2.

In one embodiment, $R^2$ is selected from one or more of the group consisting of hydrogen, deuterium, halogen, cyano, vinyl, ethynyl, $C_{1-2}$ alkyl, substituted $C_{1-2}$ alkyl, $C_{1-2}$ alkoxy, substituted $C_{1-2}$ alkoxy, $C_{1-2}$ alkylthio, substituted $C_{1-2}$ alkylthio; the substituent is selected from the group consisting of deuterium, halogen, $C_{1-2}$ alkyl, $C_{3-4}$ cycloalkyl and $C_{1-3}$ alkoxy; n is 0, 1 or 2.

In one embodiment, $R^2$ is selected from one or more of the group consisting of hydrogen, deuterium, halogen, cyano, vinyl, ethynyl, substituted or unsubstituted $C_{1-2}$ alkyl, substituted or unsubstituted $C_{1-2}$ alkoxy, substituted or unsubstituted $C_{1-2}$ alkylthio; the substituent is selected from the group consisting of deuterium, halogen, $C_{1-2}$ alkyl, $C_{3-4}$ cycloalkyl or $C_{1-3}$ alkoxy; n is 0, 1 or 2.

In a preferred embodiment, $R^2$ is selected from one or more of hydrogen, deuterium, halogen, cyano, $C_{1-2}$ alkyl, $C_{1-2}$ haloalkyl, $C_{1-2}$ alkoxy or $C_{1-2}$ alkylthio; n is 1 or 2.

In a more preferred embodiment, $R^2$ is selected from one or more of the group consisting of bromine, chlorine, and cyano, and n is 1 or 2.

In one embodiment, $R^3$ is selected from the group consisting of methyl, ethyl, n-propyl, isopropyl, cyclopropyl and cyclobutyl.

In a more preferred embodiment of the compound of the present invention or a pharmaceutically acceptable salt thereof, the compound is selected from the group consisting of:

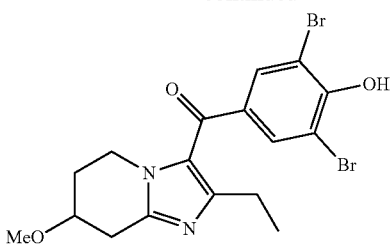

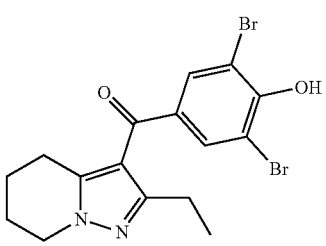

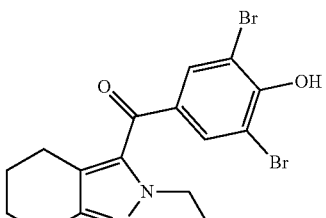

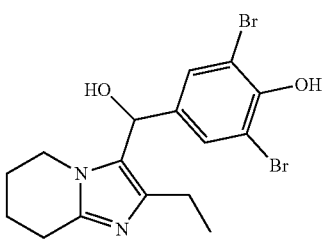

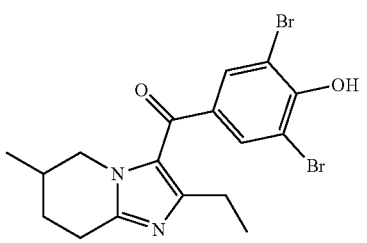

7
-continued
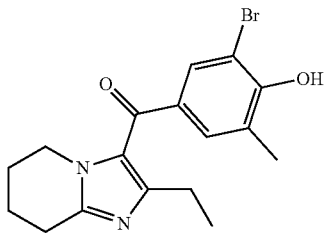
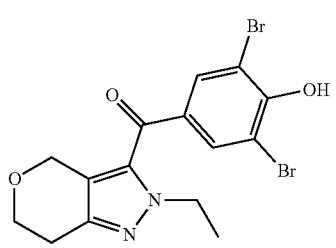
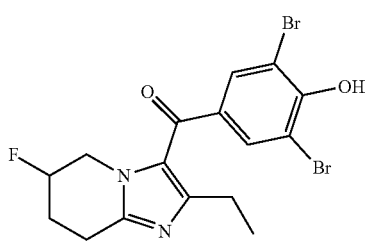
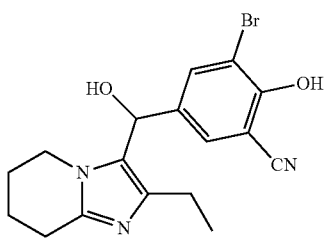
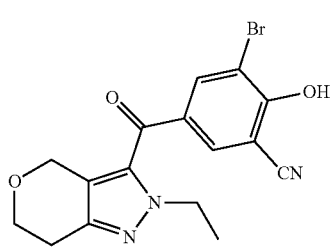
8
-continued
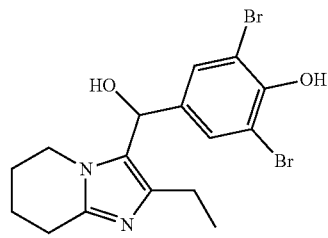
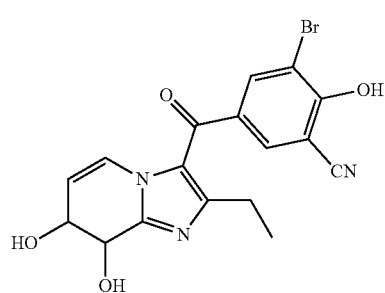
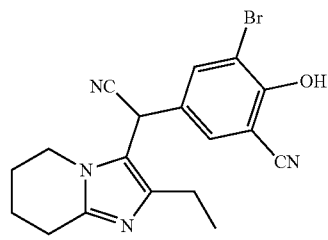
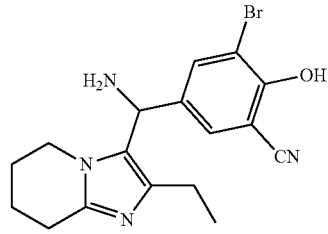
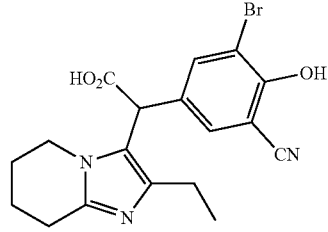

9
-continued
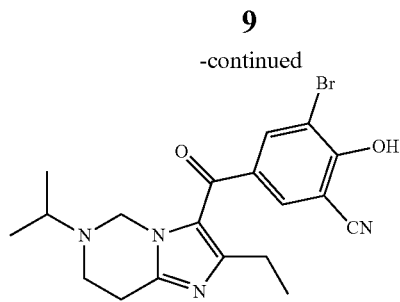
10
-continued
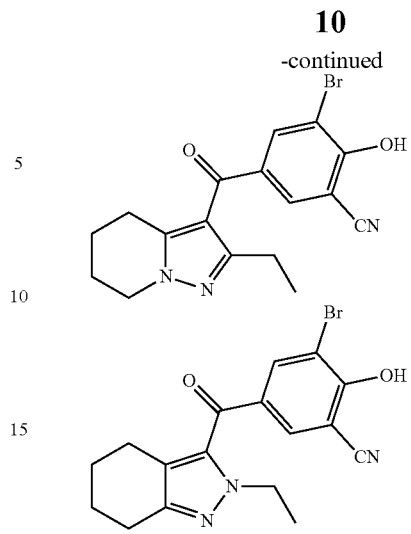
The preparation method of the compound represented by the structure of the formula (I) of the present invention includes method I and method II.
Method I:
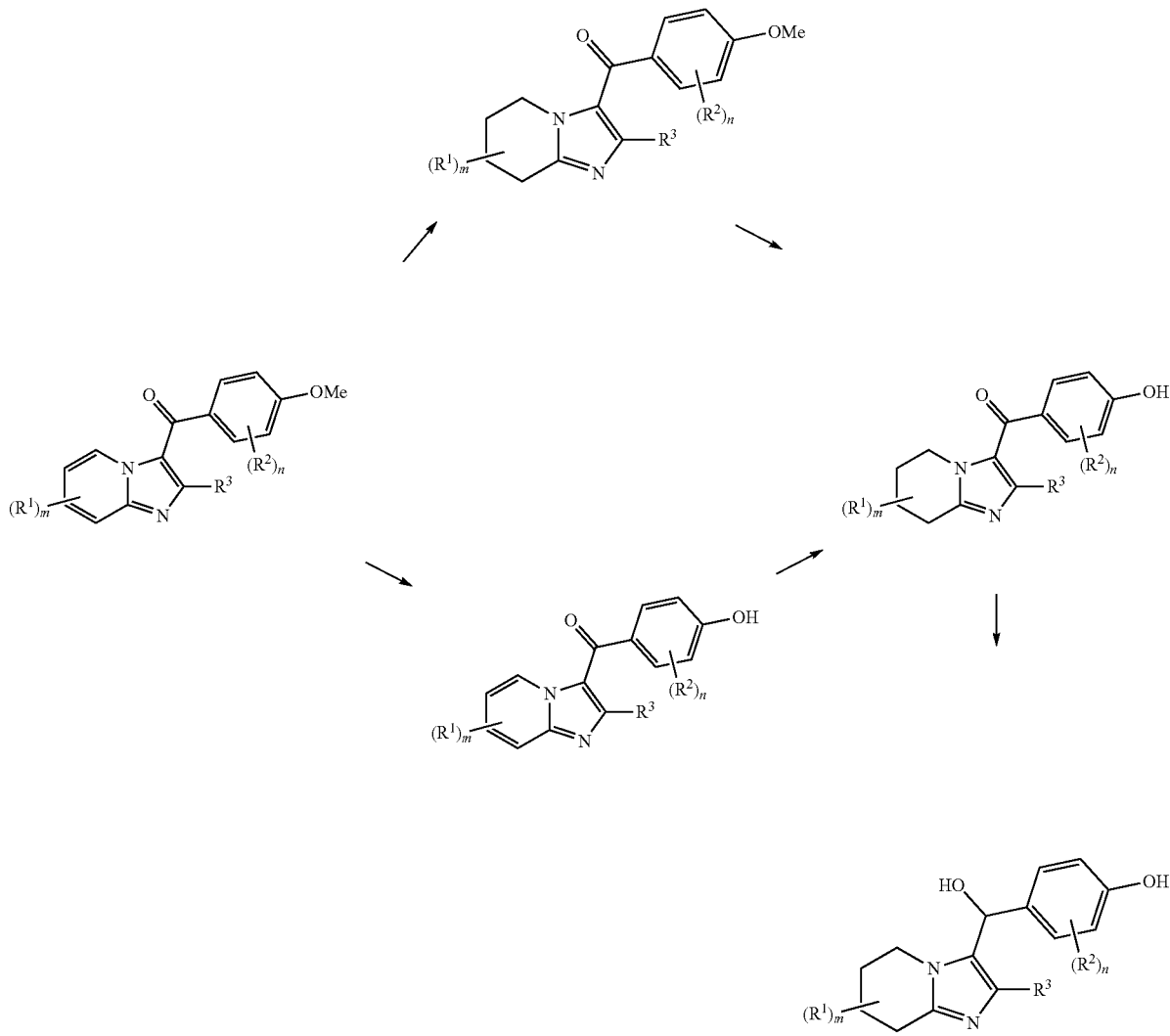

The imidazopyridine (or pyrazolopyridine) compound is subjected to a demethylation reaction and a hydrogenation (or deuteration) reaction to give a corresponding hydroxy compound, which may be a final product, or may be target product after a halogenation reaction, a reduction reaction or other reaction. $R^1$, $R^2$ and $R^3$ are as defined in the claims and the general formula of the Summary of the Invention.

Method II:

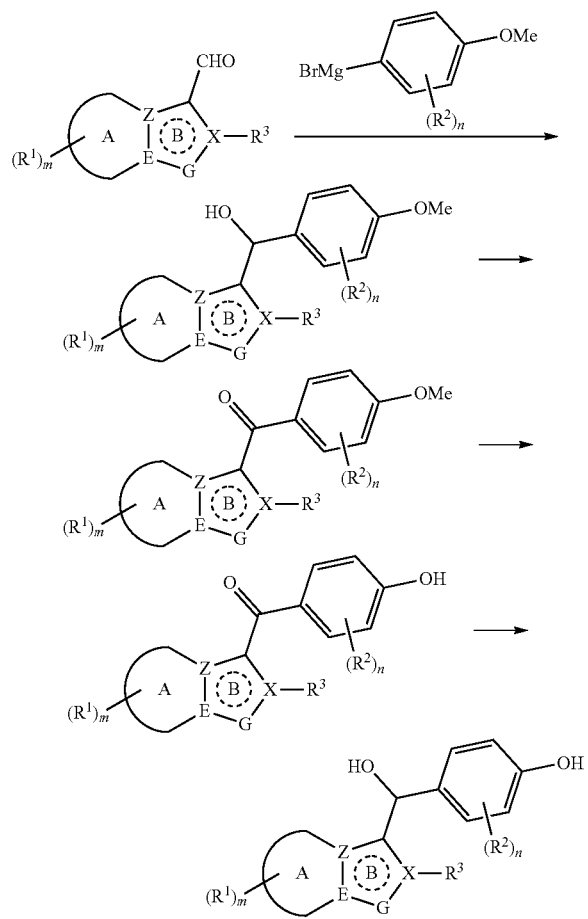

The substituted aldehyde compound is reacted with a Grignard reagent to obtain a disubstituted methanol. The disubstituted methanol is subjected to an oxidation reaction and a demethylation reaction to obtain a corresponding hydroxy compound, which may be a final product, or may be target product after a halogenation reaction, a reduction reaction or other reaction. Z, E, G, $R^1$, $R^2$ and $R^3$ are as defined in the claims and the general formula in the Summary of the Invention.

Unless otherwise stated, the following terms used in the claims and the description have the following meanings:

"Non-aromatic six-membered ring" refers to a cyclic group composed of six ring atoms, which has no aromaticity and does not belong to a six-membered aromatic ring, and the group may contain a saturated C—C single bond, may also contain unsaturated double bonds such as C=C and C=N, wherein the ring atoms may be a heteroatom other than carbon atom, such as N, S or O, etc., and the number of heteroatom is not limited to one and can be two, three, and more.

The non-aromatic six-membered ring in the present invention includes, but is not limited to, a cyclohexene ring, a 3,4-dihydro-2H-pyran ring, a 2,3,4,5-tetrahydropyridine ring, and a 5,6-di hydro-2H-1,3-oxazine ring, 1,2,5,6-tetrahydropyrimidine ring and the like.

The "five-membered aromatic ring" refers to a conjugated, planar ring-structured fused ring group composed of five ring atoms, which is aromatic and the ring atom may be an atom other than a carbon atom, i.e., hetero atom. When the five-membered aromatic ring contains a hetero atom, the hetero atom may be N, S or O, and the number of hetero atoms is not limited to one, and may be two, three or the like. The five-membered aromatic ring containing hetero atom(s) in the present invention includes, but is not limited to, a triazole ring, an imidazole ring, a thiazole ring, an oxazole ring, an oxadiazole ring or a thiadiazole ring, etc.

"Hydrogen" means protium (1H), which is the main stable isotope of hydrogen.

"Deuterium" means a stable morphological isotope of hydrogen, also known as heavy hydrogen, and its elemental symbol is D.

"Halogen" means fluorine atom, chlorine atom, bromine atom or iodine atom.

"Alkyl" means a saturated $C_{1-20}$ aliphatic hydrocarbon group, including both straight-chain and branched-chain groups (the numerical ranges recorded in this application, such as "1-20", mean the group, when it is alkyl group, may contain 1 carbon atom, 2 carbon atoms, 3 carbon atoms, etc. up to 20 carbon atoms). An alkyl group having 1 to 4 carbon atoms is referred to as a lower alkyl group. When the lower alkyl group has no substituent, it is referred to as an unsubstituted lower alkyl group. More preferably, the alkyl group is a medium sized alkyl group having 2 to 5 carbon atoms. The alkyl group in the present invention is, for example, methyl, ethyl, propyl, 2-propyl, n-butyl, isobutyl, t-butyl or pentyl. Preferably, the alkyl group is a lower alkyl group having 1 to 4 carbon atoms, such as methyl, ethyl, propyl, 2-propyl, n-butyl, isobutyl or t-butyl. The alkyl group can be substituted or unsubstituted.

"Alkoxy" means an —O— (unsubstituted alkyl) group and an —O— (unsubstituted cycloalkyl) group, which further denotes —O— (unsubstituted alkyl). Representative examples include, but are not limited to, methoxy, ethoxy, propoxy, butoxy, cyclopropoxy, cyclobutoxy, cyclopentyloxy, cyclohexyloxy, and the like.

"Carbonyl" means C=O.
"Sulfone group" means —S(O)$_2$—.
"Thionylene group" means —S(O)—.
"Methylene" means —CH$_2$—.
"Imino" means —NH—.
"Hydroxy" means —OH.
"Nitro" means —NO$_2$.
"Amino" means —NH$_2$.
"Carboxy" means —COOH.
"Cyano" means —CN.

A "pharmaceutically acceptable salt" is a salt comprising a compound of formula (I) with an organic or inorganic acid, meaning those salts which retain the biological effectiveness and properties of the parent compound. Such salts include:

(1) an acid addition salt obtained by reaction of a free base of a parent compound with an inorganic or organic acid such as, but not limited to, hydrochloric acid, hydrobromic acid, nitric acid, phosphoric acid, metaphosphoric acid, sulfuric acid, sulfurous acid and perchloric acid, etc., organic acid such as, but not limited to, acetic acid, propionic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, succinic acid or malonic acid.

(2) a salt obtained by replacing an acidic proton in a parent compound with a metal ion or by complexing with an organic base, the metal ion is, such as an alkali metal ion, an alkaline earth metal ion or an aluminum ion, the organic base is, such as ethanolamine, diethanolamine, triethanolamine, tromethamine, N-methylglucamine, and the like.

A "pharmaceutical composition" means a mixture of one or more of the compounds described herein or their pharmaceutically acceptable salts and prodrugs with other chemical ingredients, such as pharmaceutically acceptable carriers and excipients. The purpose of the pharmaceutical composition is to facilitate the administration of the compound to the organism.

Hereinafter, unless otherwise specified, the compounds of the formula (I) as active ingredients of the therapeutic agents including all pharmaceutically acceptable salts thereof, are to be understood as falling within the scope of the invention, In the present specification, they are simply referred to as "compounds of the formula (I)" for convenience only.

The present invention includes a pharmaceutical composition comprising, a compound of any one of the present invention as an active ingredient, a pharmaceutically acceptable salt thereof, or a readily hydrolyzable prodrug thereof, and as well as a pharmaceutically acceptable excipient.

Each compound of the present invention or a pharmaceutically acceptable salt thereof can be used for the manufacture of a medicament for promotion of uric acid excretion, in particular, for treatment or prevention of hyperuricemia, kidney disease or gout. Experiments show that the compounds provided by the present invention have a very good inhibitory effect on hURAT1 transport uric acid in HEK293 transfected cells, indicating that the compounds have a good application prospect in the treatment of hyperuricemia or gout.

EMBODIMENTS

The present invention will be further described below by examples, but the scope of the present invention is not limited hereinto.

Example 1

Synthesis of (3,5-dibromo-4-hydroxyphenyl)(2-ethyl-5,6,7,8-tetrahydroimidazo[1,2-a]pyridine-3-yl) methanone (5)

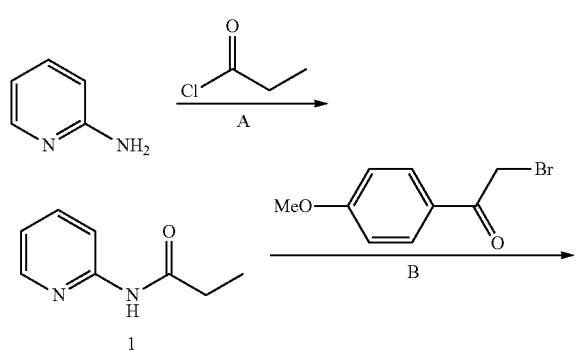

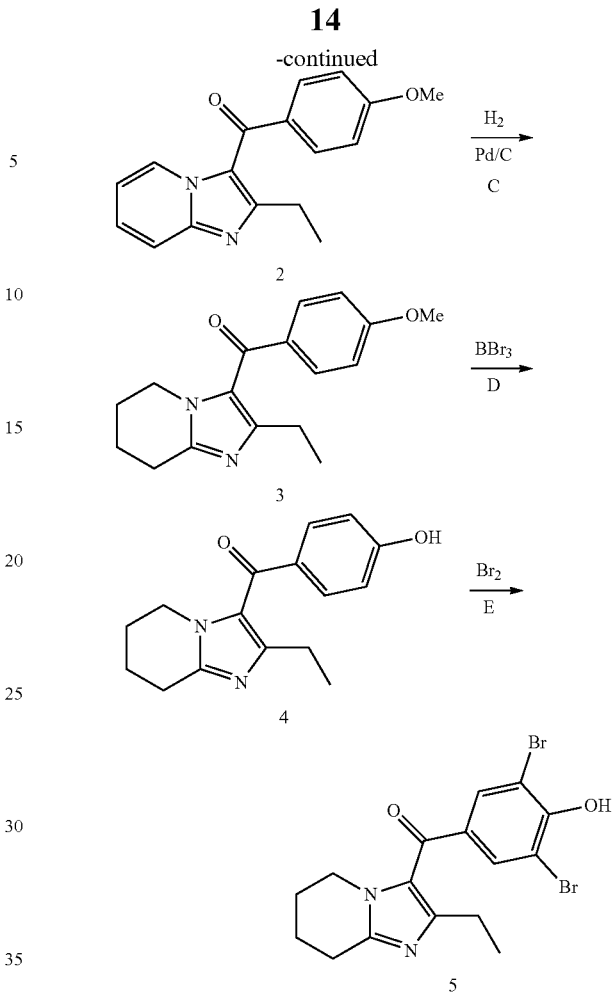

Step A: To a mixture of 2-aminopyridine (2.0 g, 21.3 mmol) and triethylamine (2.58 g, 25.5 mmol) in dichloromethane (20 mL) was added dropwise with propionyl chloride (2.07 g, 22.4 mmol) in an ice-water bath. After the addition was completed, the obtained mixture was stirred overnight at room temperature. The mixture was added with water (40 mL) and extracted with dichloromethane (40 mL×3), and the combined organic phase was washed with brine (30 mL) and dried over anhydrous sodium sulfate. The solvent was evaporated under reduced pressure, and the product was purified by flash chromatography (200-300 meshes of silica gel, eluted with ethyl acetate:petroleum ether=1:15 to 1:10) to obtain N-(pyridine-2-yl)-propionamide (1) (2.74 g). The yield was 85.6%.

Step B: A mixture containing compound 1 (300 mg, 2.0 mmol), 2-bromo-1-(4-methoxyphenyl) ethanone (460 mg, 2.0 mmol) and toluene (10 mL) was stirred under reflux for 48 hours. After cooling to room temperature, water (30 mL) was added and the pH was adjusted to 8-9 with a saturated aqueous solution of potassium carbonate. The mixture was extracted with dichloromethane (40 mL×3) and dried over anhydrous sodium sulfate. The solvent is evaporated under reduced pressure and the product is purified by column chromatography (200-300 mesh silica gel, ethyl acetate:petroleum ether=1:30 to 1:1) to give (2-ethylimidazo[1,2-a]pyridin-3-yl)(4-methoxyphenyl)methanone (2) (254 mg). The yield was 45.3%. $^1$H NMR (DMSO-$d_6$, 500 MHz) δ 9.18 (d, J=7.0 Hz, 1H), 7.74-7.69 (m, 3H), 7.58-7.55 (m, 1H), 7.17-7.14 (m, 1H), 7.09 (d, J=8.5 Hz, 2H), 3.87 (s, 3H), 2.45 (q, J=7.5 Hz, 2H), 1.11 (t, J=7.5 Hz, 3H). MS (EI, m/z): 281.1 [M+H]$^+$.

Step C: A mixture containing compound 2 (250 mg, 0.89 mmol), 10% palladium carbon (25 mg) and DMF (7 mL) was stirred overnight at 30° C. under hydrogen. Then ethyl acetate (30 mL) was added and the mixture was filtered through a celite pad. The filtrate was washed with water (30 mL×3) and dried over anhydrous sodium sulfate. The solvent was evaporated under reduced pressure to give (2-ethyl-5,6,7,8-tetrahydroimidazo[1,2-a]pyridin-3-yl)(4-methoxyphenyl)methanone (3) (230 mg). The yield was 90.7%.

Step D: To a solution of compound 3 (220 mg, 0.77 mmol) in anhydrous dichloromethane (10 mL) was added dropwise 1.0 M solution of boron tribromide in toluene (2.3 mL) in the ice water bath. After addition, the resulting mixture was stirred at room temperature overnight. The reaction mixture was poured into ice water (30 mL) and the pH was adjusted to 7-8 with saturated sodium bicarbonate. The mixture was extracted with ethyl acetate (40 mL×2) and the combined organic phases was washed with saturated brine (20 mL) and dried over anhydrous sodium sulfate. The solvent was evaporated under reduced pressure to give (2-ethyl-5,6,7,8-tetrahydroimidazo[1,2-a]pyridin-3-yl)(4-hydroxyphenyl)methanone (4) (205 mg). The yield was 98.0%.

Step E: A solution of bromine (260 mg, 1.63 mmol) in acetic acid (1 mL) was added dropwise to a mixture of compound 4 (200 mg, 0.74 mmol) and anhydrous sodium acetate (182 mg, 2.2 mmol) in acetic acid (8 mL). After the addition was completed, the resulting mixture was stirred at room temperature for 1 hour. A diluted aqueous solution of sodium bisulfite was added dropwise to the reaction mixture until the color faded. The solvent was evaporated under reduced pressure, water (15 mL) was added and then the pH value was adjusted to 7-8 with saturated sodium bicarbonate solution. The mixture was extracted with ethyl acetate (40 mL×2) and dried over anhydrous sodium sulfate. The solvent was evaporated under reduced pressure and the obtained product was recrystallized from petroleum ether/ethyl acetate to give (3,5-dibromo-4-hydroxyphenyl)(2-ethyl-5,6,7,8-tetrahydroimidazo[1,2-a]pyridin-3-yl)methanone (5) (175 mg). The yield was 55.3%. $^1$H NMR (DMSO-d$_6$, 400 MHz) δ 7.77 (s, 2H), 4.02-4.00 (m, 2H), 2.86-2.83 (m, 2H), 2.28 (q, J=7.6 Hz, 2H), 1.92-1.86 (m, 4H), 1.08 (t, J=7.6 Hz, 3H). MS (EI, m/z): 426.9 [M-H]$^-$.

Example 2

Synthesis of (3,5-dibromo-4-hydroxyphenyl)(5,6,6,7,8-pentadeuterio-2-ethyl-5,6,7,8-tetrahydroimidazo[1,2-a]pyridin-3-yl)methanone (10)

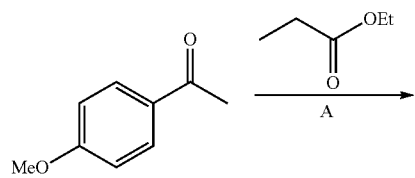

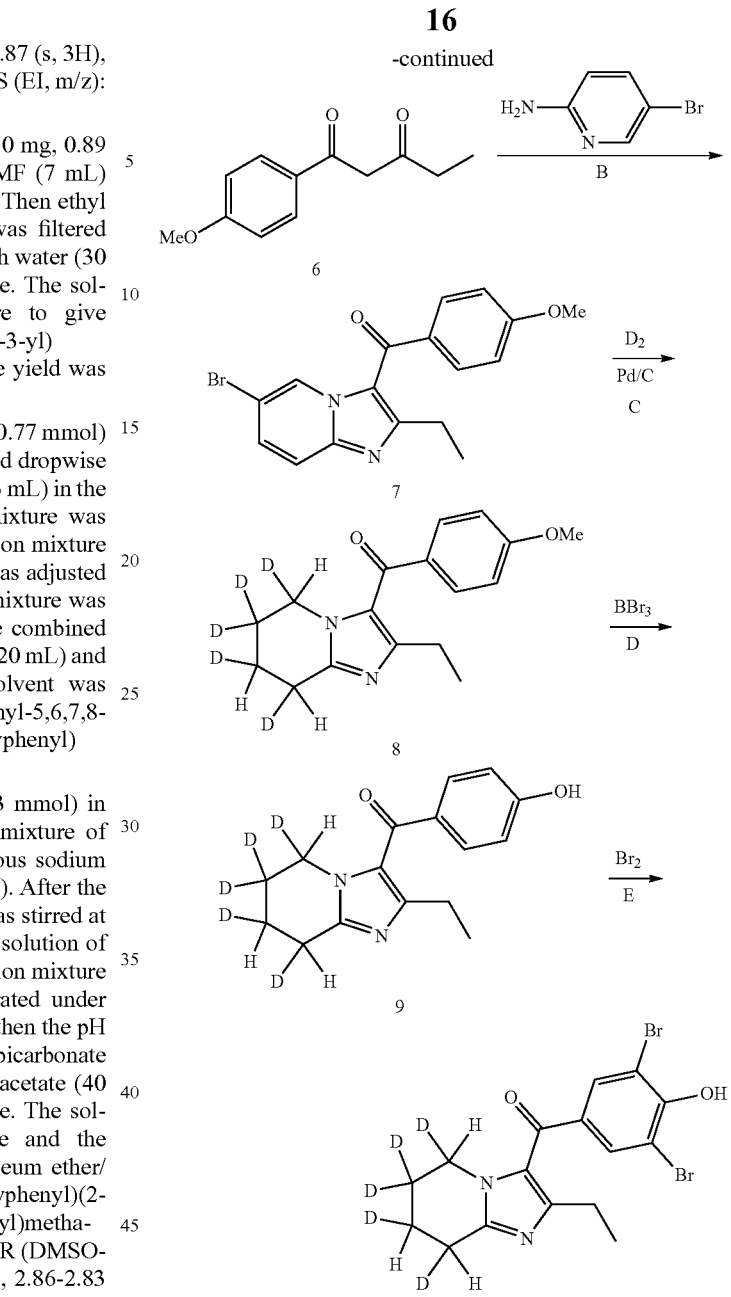

Step A: 60% sodium hydride (1.68 g, 42 mmol) was added portionwise to a solution of p-methoxyacetophenone (3.0 g, 20.0 mmol) in DMF (15 mL). After the addition was completed, stirring was continued at this temperature for 40 minutes, and then ethyl propionate (2.04 g, 20 mmol) was added dropwise. After the addition was completed, the resulting mixture was stirred at room temperature overnight. After the addition of water (60 mL), the mixture was extracted with ethyl acetate (30 mL×3), the combined organic phases was washed with saturated brine (20 mL×2) and dried over anhydrous sodium sulfate. The solvent was evaporated under reduced pressure and the product was purified by column chromatography (200-300 mesh silica gel, ethyl acetate:petroleum ether=1:30) to give 1-(4-methoxyphenyl)pentane-1,3-dione (6) (3.16 g). The yield was 76.6%.

Step B: 2-amino-5-bromopyridine (2.60 g, 15.0 mmol) and compound 6 (3.72 g, 18.0 mmol) were dissolved in THF (40 mL), and then, in the ice water bath, iodophthalic acid (5.80 g, 18.0 mmol) and boron trifluoride etherate (430 mg, 3.03 mmol)) were added sequentially. After the addition was completed, stirring was continued at room temperature overnight. Water (40 mL) was added, and the pH value was adjusted to 7-8 with a saturated sodium bicarbonate solution and then ethyl acetate (50 mL×3) was added as extraction agent. The combined organic layers was washed with saturated brine (20 mL) and dried over anhydrous sodium sulfate. The solvent was evaporated under reduced pressure, and the product was purified by column chromatography (200-300 mesh silica gel, ethyl acetate:petroleum ether=1: 20) to give (6-bromo-2-ethylimidazo[1,2-a]pyridin-3-yl)(4-methoxyphenyl)methanone (7) (1.15 g). The yield was 21.3%.

Step C: Compound 7 (200 mg, 0.557 mmol) was suspended in DMF (10 mL). Heavy water (0.5 mL) and 5% palladium on carbon (20 mg) were added, and the resulting mixture was stirred under atmospheric pressure for 48 hours under deuterium. After filtered through a celite pad, water (40 mL) was added to the filtrate, followed by extraction with ethyl acetate (30 mL×3). The combined organic phases was washed with water (20 mL×3) and dried over anhydrous sodium sulfate. The solvent was evaporated under reduced pressure to give (4-methoxyphenyl) (5,6,6,7,8-pentadeuterio-2-ethyl-5,6,7, 8-tetrahydroimidazo[1,2-a]-pyridin-3-yl)methanone (8) (164 mg). The yield was 100%. $^1$H NMR (DMSO-$d_6$, 400 MHz) δ 7.67 (dd, J=2.0, 6.8 Hz, 2H), 7.06 (dd, J=2.0, 6.8 Hz, 2H), 4.03-4.01 (m, 1H), 3.86 (s, 3H), 2.80-2.78 (m, 1H), 2.18 (q, J=7.6 Hz, 2H), 1.81-1.79 (m, 1H), 0.99 (t, J=7.6 Hz, 3H).

Experimental procedures of Steps D and E were carried out according to the preparation of Steps D and E in Example 1 to give (3,5-dibromo-4-hydroxyphenyl)(5,6,6,7, 8-pentadeuterio-2-ethyl-5,6,7,8-tetrahydroimidazo[1,2-a] pyridin-3-yl)methanone (10). $^1$H NMR (DMSO-$d_6$, 400 MHz) δ 7.80 (s, 2H), 4.05-4.01 (m, 1H), 2.85-2.83 (m, 1H), 2.27 (q, J=7.2 Hz, 2H), 1.83-1.81 (m, 1H), 1.08 (t, J=7.2 Hz, 3H). MS (EI, m/z): 434.0 [M+H]$^+$.

Example 3

Synthesis of 5-(2-ethyl-5,6,7,8-tetrahydroimidazo[1, 2-a]pyridine-3-carbonyl)-2-hydroxybenzonitrile (16)

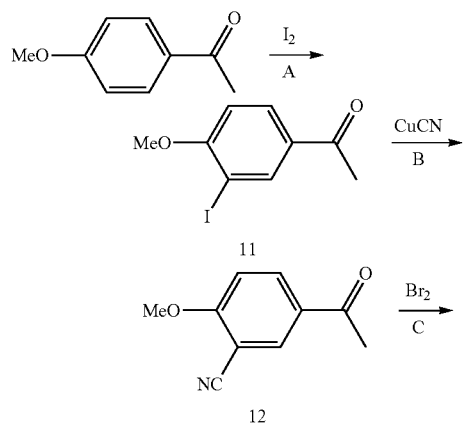

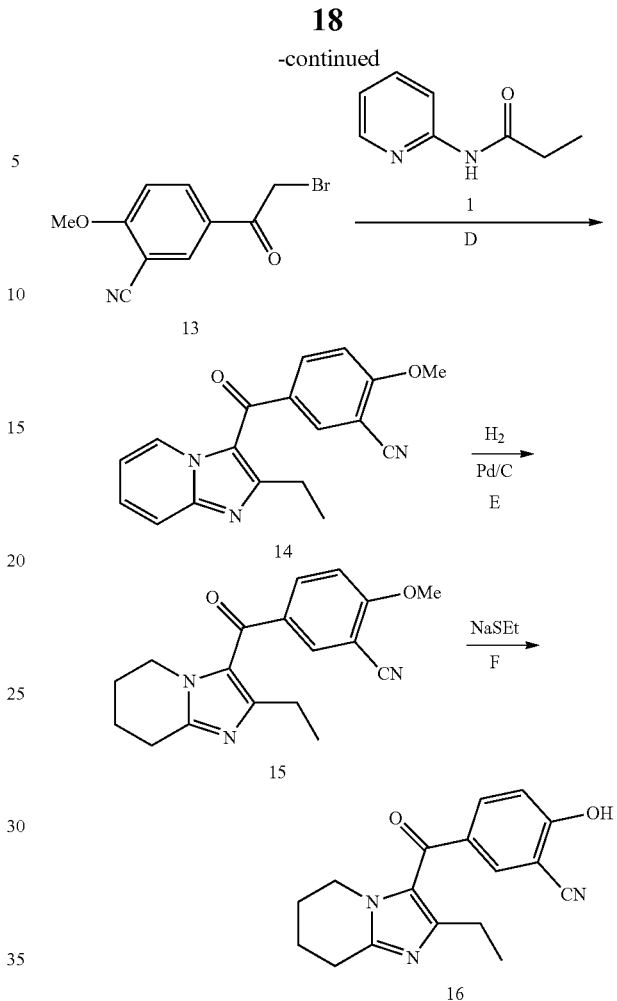

Step A: 4-methoxyacetophenone (44.0 g, 293 mmol) was added into a mixture of 1-chloromethyl-4-fluoro-1,4-diazabicyclo[2.2.2]octane bis(tetrafluoroborate) (104 g, 294 mmol), iodine (38.6 g, 152 mmol) and acetonitrile (440 mL) in an ice-water bath. After addition was completed, the obtained mixture was stirred overnight at room temperature. The reaction mixture was added with water (1350 mL), and a large amount of solid was separated out. The mixture was filtered and dried to obtain 3-iodo-4-methoxyacetophenone (11) (70.0 g). The yield was 86.5%.

Step B: A mixture of the compound 11 (70.0 g, 254 mmol), cuprous cyanide (34.0 g, 380 mmol) and DMF (400 mL) was stirred overnight at 130° C. The mixture was cooled to room temperature, filtered through a celite pad, added with water (1600 mL) and extracted with ethyl acetate (800 mL×3). The combined organic phase was successively washed with water (400 mL×2) and brine (400 mL), and then dried over anhydrous sodium sulfate. The solvent was evaporated under reduced pressure to obtain a crude compound of 5-acetyl-2-methoxybenzonitrile (12) (50.0 g). The compound was directly used in the next reaction without further treatment.

Step C: A solution of bromine (49.0 g, 307 mmol) in methanol (50 mL) was added dropwise into a solution of the crude compound 12 (45.0 g) in methanol (250 mL). After the addition was completed, the obtained mixture was stirred overnight at room temperature. The mixture was added with water (900 mL), filtered and dried to give 5-(2-bromoacetyl)-2-hydroxy-3-methylbenzonitrile(13) (41.0 g). The total yield of the reactions in the steps B and C was 70.6%.

Step D: A mixture of the compound 13 (41.0 g, 161 mmol), the compound 1 (24.0 g, 161 mmol) and methylbenzene (600 mL) was refluxed and stirred for 48 hours. The mixture was cooled to room temperature, added with water (400 mL) and adjusted with saturated sodium bicarbonate solution until the pH value was 7-8. The mixture was extracted with ethyl acetate (600 mL×3) and dried over anhydrous sodium sulfate. The solvent was evaporated under reduced pressure, and the product was purified by flash chromatography (200-300 meshes of silica gel, eluted with ethyl acetate:petroleum ether=1:30 to 2:1) to obtain 5-(2-ethylimidazo[1,2-a]pyridine-3-carbonyl)-2-methoxybenzonitrile (14) (25.7 g). The yield was 52.3%.

Step E: A mixture containing compound 14 (1.0 g, 3.28 mmol), 10% palladium carbon (100 mg) and acetic acid (10 mL) was stirred overnight at 30° C. under hydrogen atmosphere. After filtered through a celite pad, the solvent was evaporated under reduced pressure, ethyl acetate (70 mL) was added, and the mixture was washed with water (20 mL) and dried over sodium sulphate. The solvent was evaporated under reduced pressure and the product was purified by column chromatography (200-300 mesh silica gel, ethyl acetate:petroleum ether=1:3 to 4:1) to give 5-(2-ethyl-5,6,7,8-tetrahydroimidazo[1,2-a]pyridine-3-carbonyl)-2-methoxybenzonitrile (15) (400 mg). The yield was 39.5%.

Step F: 60% sodium hydride (65 mg, 1.63 mmol) was added in portions into a solution of ethanethiol (0.12 mL) in THF (10 mL), the mixture was stirred for about 5 minutes and then filtered, and the filter cake was collected. Subsequently, the filter cake was added to the solution of the compound 15 (100 mg, 0.323 mmol) in DMF (6 mL), and the obtained mixture was stirred for 1 h at 60° C. The mixture was cooled to room temperature, filtered with a celite pad, added with water (40 mL) and adjusted with 2 M citric acid aqueous solution until the pH value was 5-6. The mixture was extracted with ethyl acetate (40 mL×3) and dried over anhydrous sodium sulfate. The solvent was evaporated under reduced pressure and the product was purified by column chromatography (200-300 mesh silica gel, ethyl acetate:petroleum ether=1:2 to 5:1) to give 5-(2-ethyl-5,6,7,8-Tetrahydroimidazo[1,2-a]pyridine-3-carbonyl)-2-hydroxybenzonitrile (16) (52 mg). The yield was 54.5%. $^1$H NMR (DMSO-$d_6$, 400 MHz) δ 7.89 (s, 1H), 7.79 (dd, J=2.0, 8.8 Hz, 1H), 7.05 (d, J=8.4 Hz, 1H), 4.04 (t, J=5.6 Hz, 2H), 2.83-2.81 (m, 2H), 2.18 (q, J=7.2 Hz, 2H), 1.89-1.83 (m, 4H), 1.01 (t, J=7.2 Hz, 3H). MS (EI, m/z): 296.2 [M+H]$^+$.

Example 4

Synthesis of 3-bromo-5-(2-ethyl-5,6,7,8-tetrahydroimidazo[1,2-a]pyridine-3-carbonyl)-2-hydroxybenzonitrile (17)

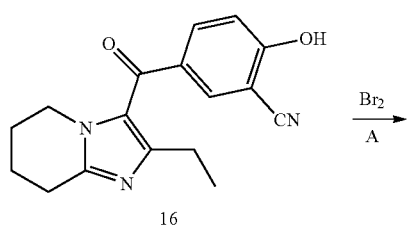

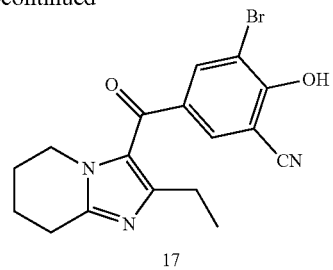

Step A: A solution of bromine (27 mg, 1.63 mmol) in acetic acid (1 mL) was added dropwise to a solution of compound 16 (50 mg, 0.74 mmol) and anhydrous sodium acetate (28 mg, 2.2 mmol) in acetic acid (8 mL) in. After the addition was completed, the resulting mixture was stirred at room temperature for 1 hour. A dilute sodium bisulfite solution was added dropwise to the reaction mixture until the color faded. The solvent was evaporated under reduced pressure, then water (15 mL) was added, and the pH value was adjusted to 7-8 with saturated sodium bicarbonate. The mixture was extracted with ethyl acetate (40 mL×2) and dried over anhydrous sodium sulfate. The solvent was evaporated under reduced pressure and the obtained product was recrystallized from petroleum ether/ethyl acetate to give 3-bromo-5-(2-ethyl-5,6,7,8-tetrahydroimidazo[1,2-a]pyridine-3-carbonyl) 2-hydroxybenzonitrile (17) (30 mg). The yield was 55.3%. $^1$H NMR (DMSO-$d_6$, 400 MHz) δ 7.93 (d, J=2.4 Hz, 1H), 7.71 (d, J=2.4 Hz, 1H), 4.00 (t, J=5.6 Hz, 2H), 2.99-2.97 (m, 2H), 2.37-2.35 (m, 2H), 1.95-1.89 (m, 4H), 1.15 (t, J=7.6, 3H). MS (EI, m/z): 376.1 [M+H]$^+$.

Example 5

Synthesis of (3,5-dibromo-4-hydroxyphenyl)(2-ethyl-7-hydroxy-5,6,7,8-tetrahydroimidazo[1,2-a]pyridine-3-yl)methanone (23) and (3,5-dibromo-4-hydroxyphenyl)-(2-ethyl-7-methoxy-5,6,7,8-tetrahydroimidazo[1,2-a]pyridin-3-yl)methanone (25)

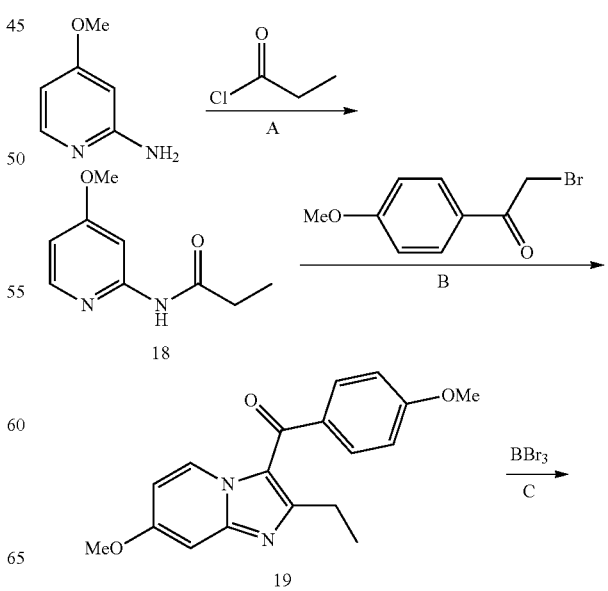

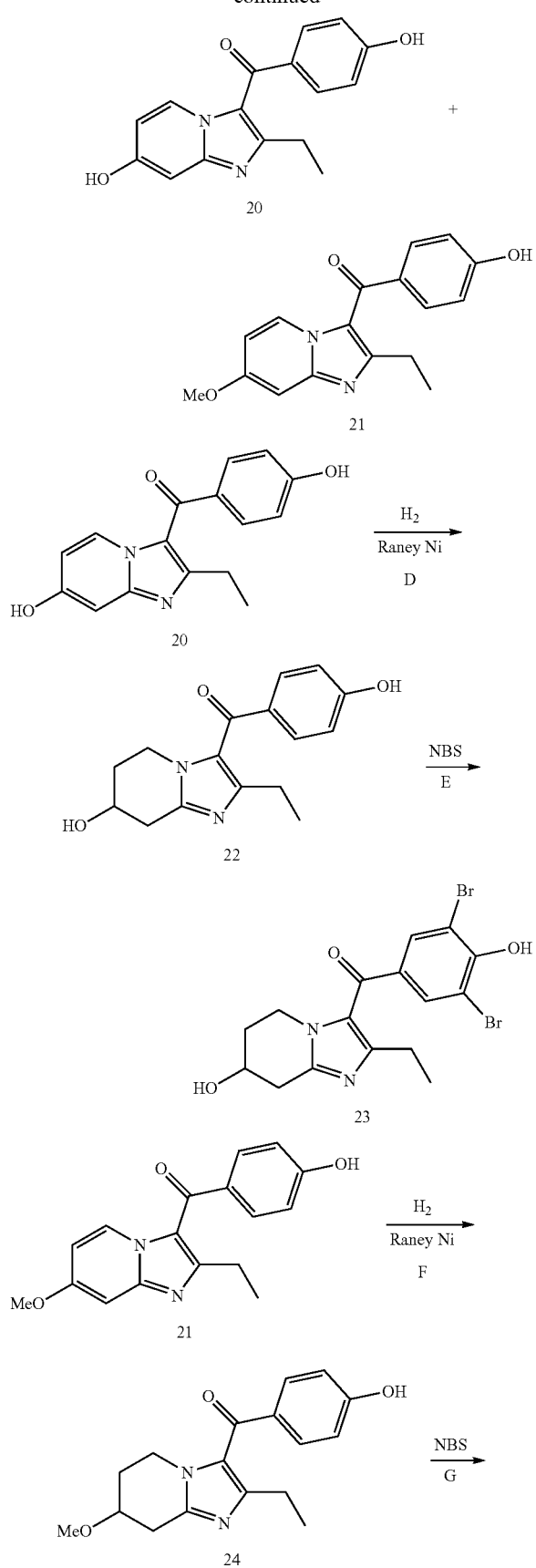
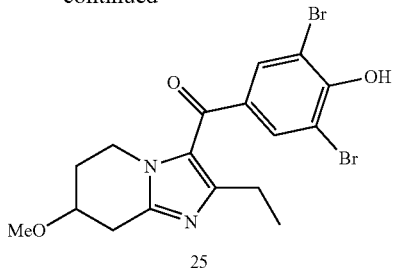

Step A: 2-amino-4-methoxypyridine (4.9 g, 39.5 mmol) and triethylamine (4.4 g, 43.5 mmol) were dissolved in tetrahydrofuran (30 mL), then propionyl chloride (4.0 g, 43.5 mmol) was added dropwise in an ice water bath, and the resulting mixture was stirred at room temperature overnight. Water (100 mL) was added, and the mixture was extracted with ethyl acetate (60 mL×3). The combined organic layers were washed with saturated brine (30 mL) and the solvent was evaporated under reduced pressure. Potassium carbonate (4.1 g, 29.7 mmol), methanol (50 mL) and water (12 mL) were added to the product, and the resulting mixture was stirred at room temperature for 1 hour. The solvent was evaporated under reduced pressure, water (20 mL) was added, the mixture was extracted with ethyl acetate (30 mL×3). The combined organic layers were washed with saturated brine (15 mL) and dried over anhydrous sodium sulfate. The solvent was evaporated under reduced pressure to give N-(4-methoxypyridin-2-yl)propanamide (18) (4.85 g). The yield was 68.2%.

Step B: A mixture containing compound 18 (4.85 g, 26.9 mmol), 2-bromo-1-(4-methoxyphenyl)ethanone (6.14 g, 26.9 mmol) and toluene (50 mL) was stirred under reflux overnight. After cooling to room temperature, water (50 mL) was added, and the pH value was adjusted to 8-9 with 2 M potassium carbonate solution. The mixture was extracted with dichloromethane (70 mL×3) and dried over anhydrous sodium sulfate. The solvent was evaporated under reduced pressure and the product was purified by column chromatography (200-300 mesh silica gel, ethyl acetate:petroleum ether=1:5 to 2:3) to give (2-ethyl-7-methoxyimidazo[1,2-a]pyridin-3-yl)(4-methoxyphenyl)methanone (19) (900 mg). The yield was 10.8%. $^1$H NMR (DMSO-$d_6$, 400 MHz) δ 9.08 (d, J=7.6 Hz, 1H), 7.67 (d, J=8.8 Hz, 2H), 7.17 (d, J=2.4 Hz, 1H), 7.08 (d, J=8.4 Hz, 2H), 6.88-6.86 (m, 1H), 3.91 (s, 3H), 3.87 (s, 3H), 2.38 (q, J=7.2 Hz, 2H), 1.10 (t, J=7.2 Hz, 3H).

Step C: A 1.0 M solution of boron tribromide in toluene (9 mL) was added dropwise to a solution of compound 19 (900 mg, 2.9 mmol) in anhydrous dichloromethane (25 mL). After the addition was completed, the resulting mixture was stirred at room temperature overnight. The reaction mixture was poured into ice water (50 mL) and the pH value was adjusted to 7-8 with saturated sodium bicarbonate. The mixture was extracted with ethyl acetate (40 mL×3) and dried over anhydrous sodium sulfate. The solvent was evaporated under reduced pressure and the product was purified by column chromatography (200-300 mesh silica gel, methanol:dichloromethane=1:50 to 1:20) to give (2-ethyl-7-hydroxyimidazo[1,2-a]pyridin-3-yl)(4-hydroxyphenyl)methanone (20) (477 mg) and (2-ethyl-7-methoxyimidazo[1,2-a]pyridine-3-yl)(4-hydroxyphenyl)methanone (21) (277 mg). The yields were 58.3% and 32.2% respectively. Compound 20: $^1$H NMR (DMSO-$d_6$, 400 MHz) δ 10.83 (s, 1H), 10.22 (s, 1H), 9.06 (d, J=7.6 Hz, 1H), 7.54 (d, J=8.4 Hz, 2H), 6.89-6.84 (m, 3H), 6.77-6.75 (m, 1H), 2.37 (q, J=7.6 Hz, 2H), 1.08 (t, J=7.6 Hz, 3H). Compound 21: $^1$H NMR (DMSO-d6, 400 MHz) δ 10.25 (s, 1H), 9.03 (d, J=7.6 Hz, 1H), 7.57 (dd, J=2.0, 6.8 Hz, 2H), 7.15 (d, J=2.4 Hz, 1H), 6.91-6.83 (m, 3H), 3.91 (s, 3H), 2.45 (q, J=7.6 Hz, 2H), 1.11 (t, J=7.6 Hz, 3H).

Step D: A mixture containing compound 20 (185 mg, 0.66 mmol), Raney Ni (40 mg) and ethanol (15 mL) was stirred under hydrogen at 60° C. for 6 hours, then Raney Ni was added to the reaction mixture (40 mg) and then stirring was continued for 3 hours at 60° C. under hydrogen. After cooled to room temperature, the mixture was filtered, and the filter cake was subject to a drip washing with a small amount of ethyl acetate. The solvent was evaporated under reduced pressure, and the product was purified by column chromatography (200-300 mesh silica gel, methanol:dichloromethane=1:50-1:30) to give (2-ethyl-7-hydroxy-5,6,7,8-tetrahydroimidazo[1,2-a]pyridin-3-yl)(4-hydroxyphenyl)methanone (22) (106 mg). The yield was 62.7%. $^1$H NMR (DMSO-d$_6$, 400 MHz) δ 10.33 (s, 1H), 7.58 (d, J=8.8 Hz, 2H), 6.86 (d, J=8.8 Hz, 2H), 5.14 (d, J=3.2 Hz, 1H), 4.17 (s, 1H), 4.12-4.02 (m, 2H), 3.02-2.96 (m, 1H), 2.74-2.68 (m, 1H), 2.20 (q, J=7.6 Hz, 2H), 1.99-1.88 (m, 2H), 1.00 (t, J=7.6 Hz, 3H).

Step E: Compound 22 (56 mg, 0.22 mmol) was dissolved in DMF (3 mL), NBS (77 mg, 0.44 mmol) was added, and the mixture was stirred in ice water bath for 0.5 hour. After the addition of water (15 mL), the mixture was extracted with ethyl acetate (30 mL×3) and the combined organic layers were washed with water (15 mL×2) and saturated brine (15 mL) and dried over anhydrous sodium sulfate. The solvent was evaporated under reduced pressure and the product was purified by column chromatography (200~300 mesh silica gel, methanol:dichloromethane=1:50) to give (3,5-dibromo-4-hydroxyphenyl)(2-ethyl-7-hydroxy-5,6,7,8-tetrahydroimidazo[1,2-a]pyridin-3-yl)methanone (23) (13 mg). The yield was 13.5%. $^1$H NMR (DMSO-d$_6$, 400 MHz) δ 7.81 (s, 2H), 5.22 (s, 1H), 4.21-4.19 (m, 1H), 4.12-4.05 (m, 2H), 3.08-3.03 (m, 1H), 2.80-2.76 (m, 1H), 2.26 (q, J=7.6 Hz, 2H), 2.03-1.19 (m, 2H), 1.07 (t, J=7.6 Hz, 3H). MS (EI, m/z): 442.9 [M–H]$^-$.

Using compound 21 as a raw material, the experimental procedures of steps F and G were carried out according to the preparation methods of steps D and E of this example to give (3,5-dibromo-4-hydroxyphenyl)(2-ethyl-7-methoxy-5,6,7,8-tetrahydroimidazo[1,2-a]pyridin-3-yl)methanone (25). $^1$H NMR (DMSO-d$_6$, 400 MHz) δ 7.81 (s, 2H), 4.09-4.03 (m, 2H), 3.88-3.87 (m, 1H), 3.33 (s, 3H), 3.07-3.06 (m, 1H), 2.94-2.93 (m, 1H), 2.24 (q, J=7.6 Hz, 2H), 2.17-2.04 (m, 2H), 1.06 (t, J=7.6 Hz, 3H). MS (EI, m/z): 457.0 [M–H]$^-$.

Example 6

Synthesis of 3,5-dibromo-4-hydroxyphenyl)(2-ethyl-4,5,6,7-tetrahydropyrazolo[1,5-a]pyridin-3-yl)methanone (32)

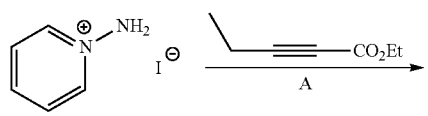

Step A: A mixture of 1-aminopyridinium iodide (15.5 g, 70.0 mmol), ethyl 2-pentynoate (9.72 g, 77.1 mmol), potassium carbonate (21.26 g, 154 mmol) and DMF (150 mL) was stirred for 4.5 hours at the room temperature. The mixture was added with water (450 mL) and filtered, and the filter cake was washed with water (100 mL) to give a wet compound of ethyl 2-ethylpyrazolo[1,5-a]-pyridine-3-formate (26) (12.25 g). The compound was directly used in the next reaction without drying.

Step B: A mixture of the wet compound 26 (12.25 g), ethanol (30 mL), THF (30 mL) and 2 M sodium hydroxide aqueous solution (70 mL) was stirred overnight at 60° C. About half of the solvent was evaporated under reduced pressure, and the mixture was added with water (150 mL) and adjusted with 2 M hydrochloric acid until the pH value was 5-6. The mixture was filtered to give a wet compound of 2-ethylpyrazolo[1,5-a]pyridine-3-formic acid (27) (10.0 g). The compound was directly used in the next reaction without drying.

Step C: The wet compound 27 (5.60 g) was suspended in water (100 mL) and added with concentrated sulfuric acid (4 mL), and the obtained mixture was stirred for 3 h at 80° C. The mixture was cooled to room temperature and adjusted with 2 M sodium hydroxide aqueous solution until the pH value was 8-9. The mixture was extracted with ethyl acetate (40 mL×3), and the combined organic phase was successively washed with water (30 mL) and brine (20 mL) and dried over anhydrous sodium sulfate. The solvent was evaporated under reduced pressure to obtain 2-ethylpyrazolo[1,5-a]pyridine (28) (3.18 g). The total yield of the reactions in the steps A, B and C was 47.7%.

Step D: A mixture of the compound 28 (584 mg, 3.99 mmol), 4-methoxybenzoyl chloride (680 mg, 3.99 mmol) and aluminum trichloride (800 mg, 6.0 mmol) was stirred overnight at 100° C. The mixture was cooled slightly, added with ethyl acetate (30 mL) and water (30 mL), and adjusted with 2 M sodium hydroxide aqueous solution until the pH value was 9-10. The mixture was layered, and the organic phase was collected. The water phase was extracted with ethyl acetate (30 mL×2), and the combined organic phase was washed with brine (20 mL) and dried over anhydrous sodium sulfate. The solvent was evaporated under reduced pressure, and the product was purified by flash chromatography (200-300 meshes of silica gel, eluted with ethyl acetate:petroleum ether=1:30 to 1:10) to obtain (2-ethylpyrazolo[1,5-a]pyridine-3-yl)(4-methoxyphenyl)methanone (29) (305 mg). The yield was 27.3%. $^1$H NMR (DMSO-$d_6$, 300 MHz) δ 8.79 (d, J=6.9 Hz, 1H), 7.66 (d, J=8.7 Hz, 2H), 7.44-7.39 (m, 1H), 7.33-7.30 (m, 1H), 7.08-7.03 (m, 3H), 3.86 (s, 3H), 2.84 (q, J=7.5 Hz, 2H), 1.20 (t, J=7.5 Hz, 3H).

Step E: 60% sodium hydride (218 mg, 5.45 mmol) was added in portions into a solution of ethanethiol (338 mg, 5.44 mmol) in DMF (3 mL), the reaction mixture was stirred for about 5 minute and then added with a solution of the compound 29 (305 mg, 1.09 mmol) in DMF (3 mL), and the obtained mixture was stirred for 2 hours at 120° C. The mixture was cooled to room temperature, added with water (30 mL) and adjusted with diluted hydrochloric acid until the pH value was 7-8. Subsequently, the mixture was extracted with ethyl acetate (30 mL×3), and the combined organic phase was successively washed with water (20 mL×3) and brine (20 mL) and dried over anhydrous sodium sulfate. The solvent was evaporated under reduced pressure to obtain (2-ethylpyrazolo[1,5-a]pyridine-3-yl)(4-hydroxyphenyl)methanone (30) (420 mg). The compound was directly used in the next reaction without purification. $^1$H NMR (DMSO-$d_6$, 300 MHz) δ 10.27 (s, 1H), 8.76 (d, J=6.6 Hz, 1H), 7.56 (d, J=8.4 Hz, 2H), 7.42-7.31 (m, 2H), 7.05-7.01 (m, 1H), 6.87 (d, J=8.4 Hz, 2H), 2.84 (q, J=7.5 Hz, 2H), 1.20 (t, J=7.5 Hz, 3H).

Step F was carried out according to the preparation method of Step D in Example 4 to give (2-ethyl-4,5,6,7-tetrahydropyrazolo[1,5-a]pyridin-3-yl)(4-hydroxyphenyl)methanone (31).

Step G: NBS (86 mg, 0.483 mmol) was added to a solution of compound 31 (65 mg, 0.240 mmol) in DMF (5 mL) and stirred for 1 hour. After the addition of water (20 mL), the mixture was extracted with ethyl acetate (20 mL×3), and the combined organic phases were washed with water (10 mL×3) and saturated brine (10 mL) and dried over sodium sulphate. The solvent was evaporated under reduced pressure, and the product was purified by column chromatography (200-300 mesh silica gel, ethyl acetate:dichloromethane=1:10) to give 2-ethyl-4,5,6,7-tetrahydropyrazolo[1,5-a]pyridin-3-yl)methanone (32). $^1$H NMR (DMS O-$d_6$, 400 MHz) δ 7.74 (s, 2H), 4.05 (t, J=6.0 Hz, 2H), 3.36-3.34 (m, 2H), 2.57-2.51 (m, 2H), 1.96-1.95 (m, 2H), 1.72-1.70 (m, 2H), 1.08 (t, J=7.6 Hz, 3H). MS (EI, m/z): 429.0 [M+H]$^+$.

Example 7

Synthesis of (3,5-dibromo-4-hydroxyphenyl)(2-ethyl-4,5,6,7-tetrahydro-2H-indazol-3-yl)methanone (41)

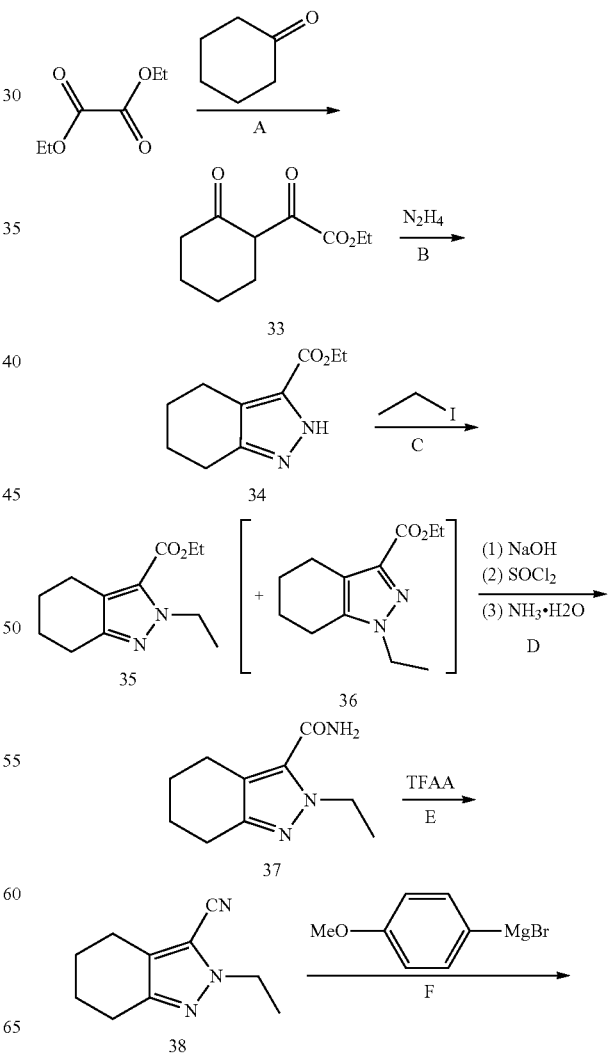

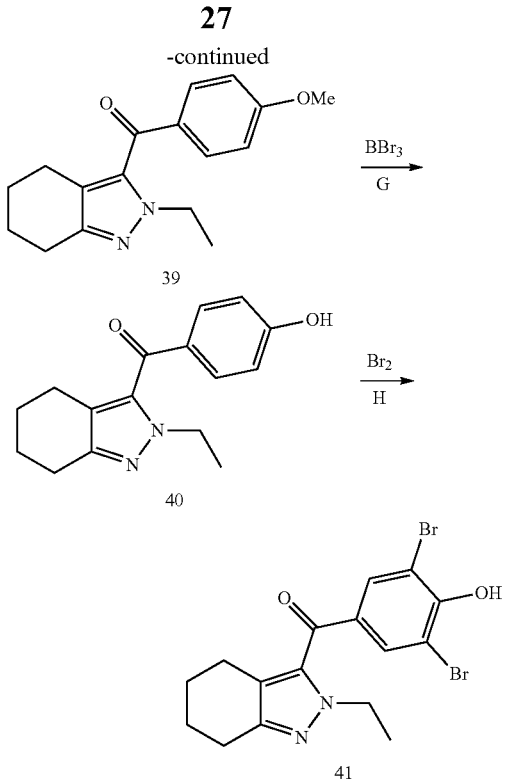

Step A: To a solution of cyclohexanone (9.81 g, 100 mmol) and diethyl oxalate (14.6 g, 100 mmol) in THF (100 mL) was added portionwise 60% sodium hydride (4.8 g, 120 mmol). After the addition was completed, the mixture was heated to 40° C. and stirred for 0.5 hour, and then raised to 50° C. and stirred for 1.5 hours. After cooling to room temperature, the reaction solution was poured into a solution of acetic acid (8 mL) in water (200 mL). The mixture was extracted with methyl tert-butyl ether (100 mL×2), and the combined organic phases were washed with saturated brine (40 mL). The solvent was evaporated under reduced pressure and the product was purified by column chromatography (200-300 mesh silica gel, eluted with petroleum ether) to give ethyl 2-oxy-2-(2-oxocyclohexyl)acetate (33) (10.5 g). The yield was 53.0%.

Step B: A solution of compound 33 (10.1 g, 51.0 mmol) and 85% hydrazine hydrate (1.84 g, 48.8 mmol) in ethanol (40 mL) was stirred at 60° C. for 2 hours. The solvent was evaporated under reduced pressure, water (40 mL) was added, the mixture was extracted with ethyl acetate (40 mL×3) and the combined organic layers was washed with brine (30 mL). The solvent was evaporated under reduced pressure and the product was purified by column chromatography (200-300 mesh silica gel, petroleum ether:ethyl acetate=1:100 to 1:3) to give 4,5,6,7-tetrahydro-2H-indazole-3-carboxylic acid ethyl ester (34) (5.0 g). The yield was 50.5%.

Step C: A mixture containing compound 34 (2.3 g, 11.8 mmol), ethyl iodide (3.69 g, 23.7 mmol), cesium carbonate (5.79 g, 17.8 mmol) and DMF (25 mL) was stirred at room temperature overnight. After the addition of water (75 mL), the mixture was extracted with ethyl acetate (50 mL×3) and the combined organic layers was washed with water (20 mL×2) and saturated brine (15 mL) and dried over anhydrous sodium sulfate. The solvent was evaporated under reduced pressure and the product was purified by column chromatography (200-300 mesh silica gel, petroleum ether: ethyl acetate=1:20 to 1:10) to give 2-ethyl-4,5,6,7-tetrahydro-2H-indazole-3-carboxylic acid ethyl ester (35) (1.58 g, petroleum ether:ethyl acetate=1:1, $R_f$=0.8) and 1-ethyl-4,5,6,7-tetrahydro-2H-indazole-3-carboxylic acid ethyl ester (36) (1.01 g, petroleum ether:ethyl acetate=1:1, $R_f$=0.5). The yields were 60.2% and 38.5% respectively.

Step D: A mixture containing compound 35 (1.58 g, 7.24 mmol), sodium hydroxide (580 mg, 14.5 mmol), methanol (5 mL) and water (15 mL) was stirred at 40° C. for 1 hour. The water was evaporated under reduced pressure, and then water was carried twice with toluene. Thionyl chloride (6 mL) and DMF (1 drop) were added to the residue, and the resulting mixture was stirred under reflux for 1 hour. The solvent was evaporated under reduced pressure, then THF (15 mL) was added, and the above THF solution was added portionwise to a concentrated aqueous ammonia (15 mL) in an ice water bath. After the addition was completed, stirring was continued for 20 minutes. After added water (30 mL), the mixture was extracted with ethyl acetate (30 mL×3) and the combined organic layers was washed with brine (20 mL) and dried over anhydrous sodium sulfate. The solvent was evaporated under reduced pressure to give 2-ethyl-4,5,6,7-tetrahydro-2H-indazole-3-carboxamide (37) (1.18 g). The yield was 84.3%.

Step E: A solution of trifluoroacetic anhydride (1.92 g, 9.14 mmol) and compound 37 (1.1 g, 5.69 mmol) in THF (20 mL) was stirred at room temperature for 3 hours. The solvent was evaporated under reduced pressure, water (20 mL) was added, and the pH value was adjusted to 8-9 with a 2 M aqueous sodium hydroxide solution. The mixture was extracted with ethyl acetate (30 mL×2) and the combined organic layers was washed with brine (15 mL) and dried over anhydrous sodium sulfate. The solvent was evaporated under reduced pressure, and the product was purified by column chromatography (200-300 mesh silica gel, ethyl acetate:petroleum ether=1:20) to give 2-ethyl-4,5,6,7-tetrahydro-2H-indazole-3-carbonitrile (38) (640 mg). The yield was 64.2%. 1H NMR (DMSO-d6, 400 MHz) δ 4.22 (q, J=7.2 Hz, 2H), 2.59-2.50 (m, 4H), 1.76-1.68 (m, 4H), 1.37 (t, J=7.2 Hz, 3H).

Step F: 1.0 M of 4-methoxyphenylmagnesium bromide in THF (5.7 mL) was added dropwise to a solution of compound 38 (500 mg, 2.85 mmol) in THF (10 mL). After the addition was completed, the resulting mixture was stirred at room temperature overnight. 6 M hydrochloric acid solution (5 mL) was added, and the pH value was adjusted to 8-9 with a 2 M aqueous sodium hydroxide solution after stirring for about 1 hour. The mixture was extracted with ethyl acetate (40 mL×2) and the combined organic layers was washed with brine (20 mL) and dried over anhydrous sodium sulfate. The solvent was evaporated under reduced pressure, and the product was purified by column chromatography (200-300 mesh silica gel, ethyl acetate:petroleum ether=1:100 to 1:1) to give (2-ethyl-4,5,6,7-tetrahydro-2H-indazol-3-yl)(4-methoxyphenyl)methanone (39) (300 mg). The yield was 37.0%.

Step G: A 1.0 M solution of boron tribromide in toluene (3.2 mL) was added dropwise to a solution of compound 39 (300 mg, 1.05 mmol) in anhydrous dichloromethane (6 mL). After addition, the resulting mixture was stirred at room temperature overnight. The reaction mixture was poured into ice water (30 mL) and the pH value was adjusted to 7-8 with saturated sodium bicarbonate. The mixture was extracted with ethyl acetate (30 mL×3) and the combined organic layers was washed with brine (20 mL) and dried over anhydrous sodium sulfate. The solvent was evaporated under reduced pressure to give (2-ethyl-4,5,6,7-tetrahydro- 2H-indazol-3-yl)(4-hydroxyphenyl)methanone (40) (280 mg). The yield was 98.6%. ¹H NMR (DMSO-d₆, 400 MHz) δ 10.22 (s, 1H), 7.38 (d, J=8.4 Hz, 2H), 6.81 (d, J=8.4 Hz, 2H), 3.99-3.96 (m, 2H), 2.58-2.55 (m, 2H), 2.10-2.08 (m, 2H), 1.72-1.70 (m, 2H), 1.58-1.57 (m, 2H), 1.21 (t, J=7.2 Hz, 3H).

Step H: A solution of bromine (124 mg, 0.776 mmol) in acetic acid (3 mL) was added dropwise to a mixture of compound 40 (100 mg, 0.370 mmol) and anhydrous sodium acetate (89 mg, 1.11 mmol) in acetic acid (15 mL). After the addition was completed, the resulting mixture was stirred at room temperature for 1 hour. A diluted aqueous solution of sodium bisulfite was added dropwise to the reaction mixture until the color faded. The solvent was evaporated under reduced pressure, water (15 mL) was added, and the pH value was adjusted to 7-8 with saturated sodium bicarbonate. The mixture was extracted with ethyl acetate (40 mL×2) and dried over anhydrous sodium sulfate. The solvent was evaporated under reduced pressure, and the product was purified by column chromatography (200-300 mesh silica gel, ethyl acetate:petroleum ether=1:100 to 1:1) to give (3,5-dibromo-4-hydroxyphenyl) (2-ethyl-4,5,6,7-tetrahydro-2H-indazol-3-yl)methanone (41). ¹H NMR (DMSO-d₆, 400 MHz) δ 7.83 (s, 2H), 4.20-4.18 (m, 2H), 2.60-2.58 (m, 2H), 2.14-2.11 (m, 2H), 1.73-1.72 (m, 2H), 1.57-1.56 (m, 2H), 1.31 (t, J=7.2 Hz, 3H). MS (EI, m/z): 426.9 [M−H]⁻.

Example 8

Synthesis of 2,6-dibromo-4-[(2-ethyl-5,6,7,8-tetrahydroimidazo[1,2-a]-pyridin-3-yl)hydroxymethyl]phenol (42)

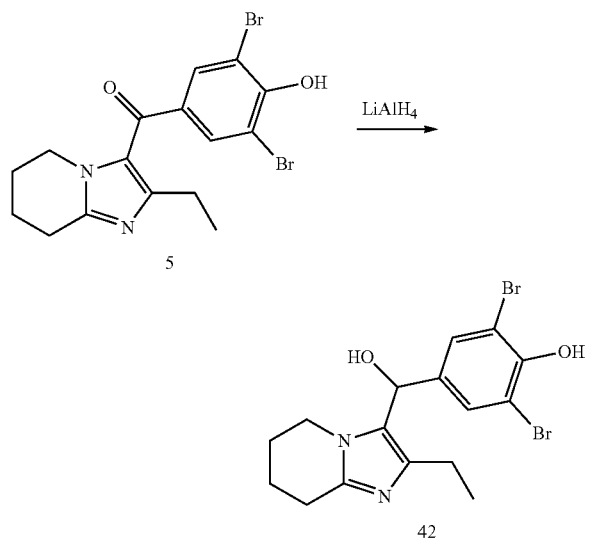

Lithium aluminum hydride (18 mg, 0.474 mmol) was added to a solution of compound 5 (135 mg, 0.315 mmol) in THF (15 mL), and the mixture was stirred at this temperature for 0.5 hour. After adding water (15 mL), the pH value was adjusted to 5-6 with 2 M citric acid solution, and the mixture was extracted with ethyl acetate/THF mixture (20 mL×3). The combined organic phases was washed with brine (15 mL) and dried over anhydrous sodium sulfate. The solvent was evaporated under reduced pressure and the product was purified by column chromatography (200-300 mesh silica gel, dichloromethane:methanol=1:100 to 1:30) to give 2,6-dibromo-4-[(2-ethyl-5,6,7,8-tetrahydroimidazo[1,2-a]pyridin-3-yl)-hydroxymethyl]phenol (42). ¹H NMR (DMSO-d₆, 400 MHz) δ 7.36 (s, 2H), 5.95 (s, 1H), 5.78 (s, 1H), 3.88-3.85 (m, 2H), 2.67-2.65 (m, 2H), 2.32 (q, J=7.6 Hz, 2H), 1.76-1.69 (m, 4H), 1.04 (t, J=7.6 Hz, 3H). MS (EI, m/z): 431.0 [M+H]⁺.

Example 9

Synthesis of (3,5-dibromo-4-hydroxyphenyl)(2-ethyl-6-methyl-5,6,7,8-tetrahydroimidazo[1,2-a]pyridin-3-yl)methanone (43)

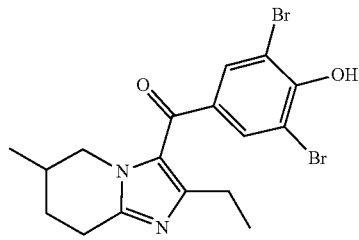

43

The synthesis of Compound 43 was carried out according to the procedures of Example 1, in which 2-aminopyridine in Step A of Example 1 was replaced with 2-amino-5-methylpyridine. ¹H NMR (DMSO-d₆, 400 MHz) δ 7.79 (s, 2H), 4.16-4.11 (m, 1H), 3.57-3.51 (m, 1H), 2.96-2.79 (m, 2H), 2.27 (q, J=7.6 Hz, 2H), 2.03-1.91 (m, 2H), 1.56-1.47 (m, 1H), 1.09-1.03 (m, 6H). MS (EI, m/z): 441.0 [M−H]⁻.

Example 10

Synthesis of (3-bromo-4-hydroxy-5-methylphenyl)(2-ethyl-5,6,7,8-tetrahydroimidazo[1,2-a]pyridin-3-yl)methanone (48)

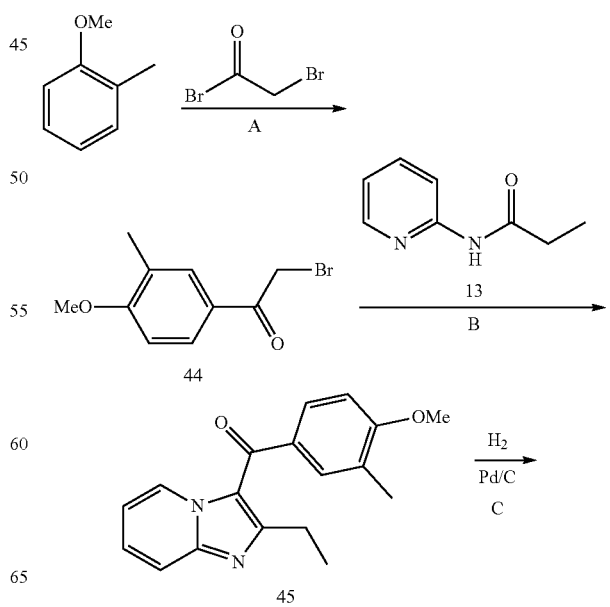

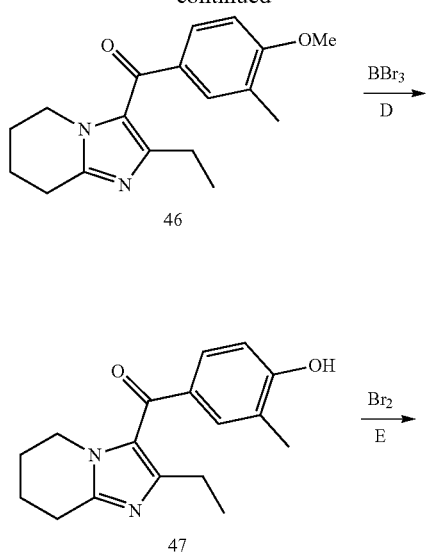

Step A: A solution of bromoacetyl bromide (9.9 g, 49.0 mmol) in dichloromethane (10 mL) was added dropwise into a solution of 2-methylanisole (5.0 g, 40.9 mmol) and aluminum trichloride (6.0 g, 45.0 mmol) in dichloromethane (40 mL) for about 20 minute at 0-5° C. After the addition was completed, the obtained mixture was continuously stirred for 2 hours at this temperature. The reaction solution was poured into a proper amount of ice water in batches and extracted with dichloromethane (60 mL×3). The combined organic phase was successively washed with water (30 mL), saturated sodium bicarbonate aqueous solution (30 mL×2), water (30 mL) and brine (30 mL) and then dried over anhydrous sodium sulfate. The organic phase was filtered by a short silica gel column. The solvent was evaporated under reduced pressure, and the product was purified by flash chromatography (200-300 meshes of silica gel, ethyl acetate:petroleum ether=1:100 to 1:30) to obtain 2-bromo-1-(3-methyl-4-methoxyphenyl)ethanone (44) (3.0 g). The yield was 30.2%.

Steps B, C, D and E were carried out according to the preparation of Steps B, C, D and E in Example 1 to give (3-bromo-4-hydroxy-5-methylphenyl)(2-ethyl-5,6,7,8-tetrahydroimidazo[1,2-a]pyridin-3-yl)methanone (48). $^1$H NMR (DMSO-$d_6$, 400 MHz) δ 7.57 (s, 1H), 7.28 (s, 1H), 3.89-3.87 (m, 2H), 2.76-2.73 (m, 2H), 2.29 (q, J=7.6 Hz, 2H), 1.96 (s, 3H), 1.87-1.80 (m, 4H), 1.05 (q, J=7.6 Hz, 3H). MS (EI, m/z): 363.1 [M+H]$^+$.

Example 11

Synthesis of (3,5-dibromo-4-hydroxyphenyl)(2-ethyl-2,4,6,7-tetrahydropyrano[4,3-c]pyrazol-3-yl methanone (58)

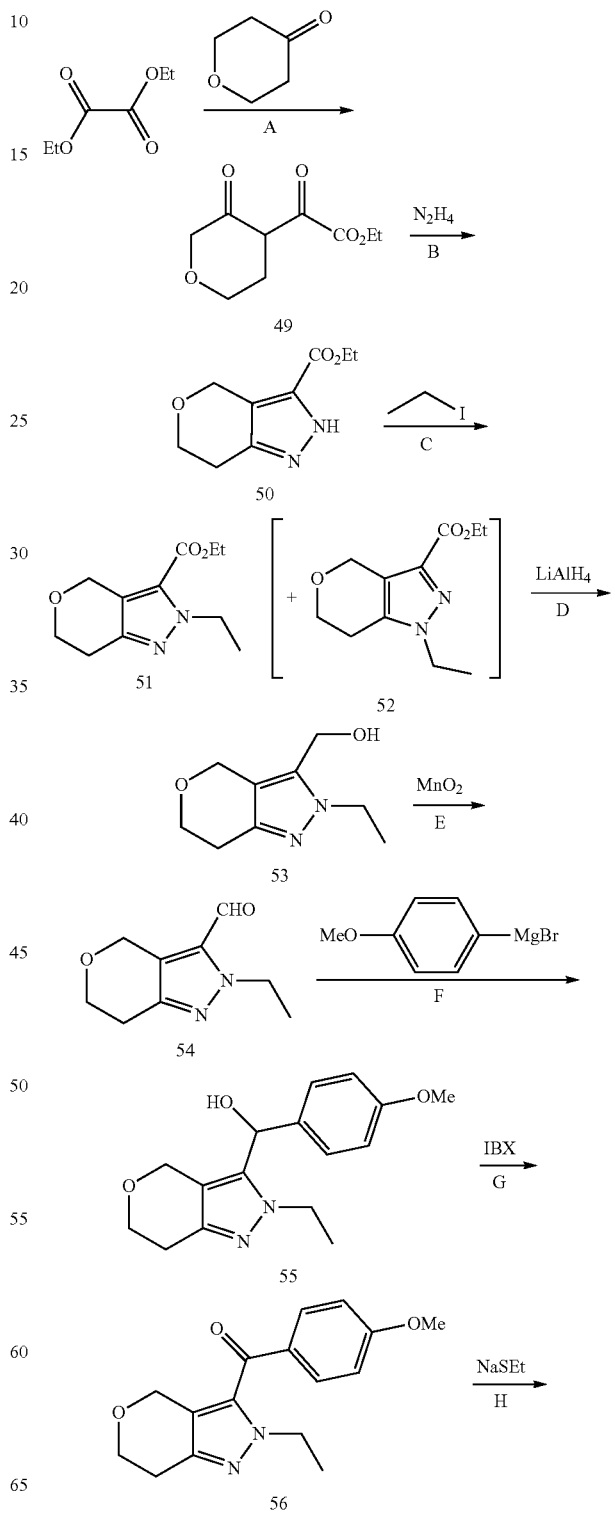

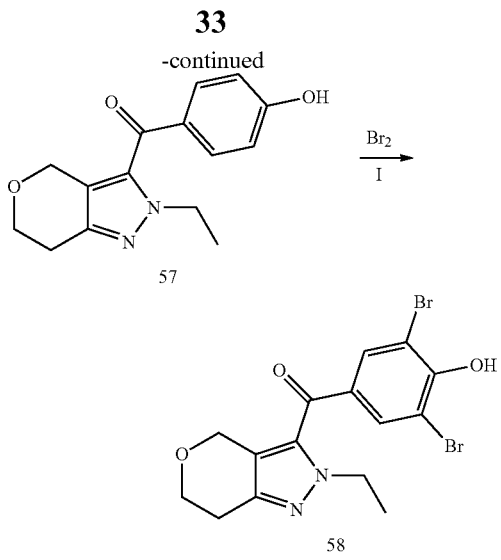

solvent was evaporated under reduced pressure to give (2-ethyl-2,4,6,7-tetrahydropyrano[4,3-c]pyrazol-3-yl)(4-methoxyphenyl)-methanone (56) (1.32 g). The yield was 96.3%.

Step H Experimental procedures were carried out according to the preparation method of Step F in Example 3 to give (2-ethyl-2,4,6,7-tetrahydropyrano[4,3-c]pyrazol-3-yl)(4-hydroxyphenyl)methanone (57).

Step I Experimental procedures were carried out according to the preparation method of Step E in Example 1 to give (3,5-dibromo-4-hydroxyphenyl)(2-ethyl-2,4,6,7-tetrahydropyran)-[4,3-c]pyrazol-3-yl)methanone (58). $^1$H NMR (DMSO-d$_6$, 400 MHz) δ 7.84 (s, 2H), 4.26 (q, J=7.2 Hz, 2H), 4.22 (s, 2H), 3.86 (t, J=6.4 Hz, 2H), 2.71 (t, J=6.4 Hz, 2H), 1.35 (t, J=7.2 Hz, 3H). MS (EI, m/z): 431.0 [M+H]$^+$.

Example 12

Synthesis of (3,5-dibromo-4-hydroxyphenyl)(2-ethyl-6-fluoro-5,6,7,8-tetrahydroimidazo[1,2-a]pyridine-3-yl)methanone (62)

Experimental procedures of Steps A, B, and C were carried out according to the preparation of Steps A, B, and C in Example 7, wherein the cyclohexanone in Step A of Example 1 was replaced with tetrahydropyrone.

Step D: A solution of compound 51 (2.5 g, 11.1 mmol) in THF (10 mL) was added dropwise to a mixture containing lithium aluminum hydride (846 mg, 22.3 mmol) and THF (15 mL). After the addition was completed, the resulting mixture was further stirred at this temperature for 1 hour. Water (1 mL), 10% sodium hydroxide solution (2 mL) and water (3 mL) were added dropwise to the reaction mixture. After filtrated, the filter cake was subject to a drip washing with THF (15 mL) and the filtrate was dried over anhydrous sodium sulfate. The solvent was evaporated under reduced pressure to give (2-ethyl-2,4,6,7-tetrahydropyrano[4,3-c]pyrazol-3-yl)methanol (53) (2.1 g). The yield was 100%.

Step E: A mixture containing compound 53 (2.0 g, 11.0 mmol), manganese dioxide (4.78 g, 55.0 mmol) and chloroform (15 mL) was stirred at 45° C. overnight. The insolubles were removed by filtration, and the solvent was evaporated under reduced pressure. The product was purified by column chromatography (200-300 mesh silica gel, ethyl acetate:petroleum ether=1:20 to 1:6) to give (2-ethyl-2,4,6,7-tetrahydropyrano[4,3-c]pyrazol-3-yl)carbaldehyde (54) (928 mg). The yield was 46.8%.

Step F: 1.0 M solution of 4-methoxyphenylmagnesium bromide in THF (5.5 mL) was added dropwise to a solution of compound 54 (900 mg, 4.99 mmol) in THF (15 mL) at −70° C. After the addition was completed, the resulting mixture was stirred at this temperature for further 20 minutes. The reaction mixture was slowly added dropwise to ice water (20 mL), and extracted with ethyl acetate (30 mL×3). The combined organic phases were dried over brine (30 mL) and dried over anhydrous sodium sulfate. The solvent was evaporated under reduced pressure and the product was purified by column chromatography (200-300 mesh silica gel, ethyl acetate:petroleum ether=1:10 to 1:1) to give (2-ethyl-2,4,6,7-tetrahydropyrano[4,3-c]pyrazol-3-yl)(4-methoxyphenyl)methanol (55) (1.4 g). The yield was 97.3%.

Step G: A mixture containing compound 55 (1.38 g, 4.79 mmol), 2-iodobenzoic acid (1.74 g, 55.0 mmol) and DMSO (15 mL) was stirred at room temperature for 1.5 hours. After the addition of water (45 mL), the mixture was extracted with ethyl acetate (30 mL×3) and the combined organic phases were washed successively with water (20 mL×2) and brine (20 mL) and dried over anhydrous sodium sulfate. The

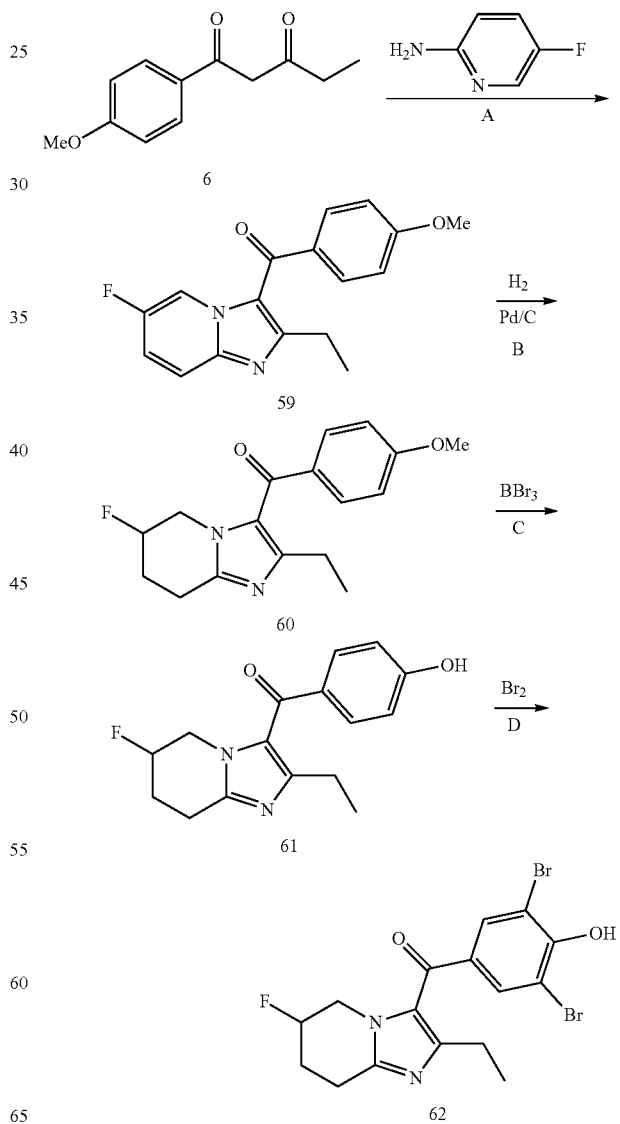

Step A: 2-amino-5-fluoropyridine (750 mg, 6.69 mmol) and compound 6 (1.65 g, 8.00 mmol) were dissolved in THF (15 mL), then, iodophthalic acid (2.59 g, 8.05 mmol) and boron trifluoride etherate (192 mg, 1.35 mmol)) were added sequentially in the ice water bath. After the addition was completed, stirring was continued at room temperature overnight. Water (30 mL) was added, and the pH value was adjusted to 7-8 with a saturated sodium bicarbonate solution and then the mixture was extracted with ethyl acetate (30 mL×3). The combined organic layers was washed with brine (20 mL) and dried over anhydrous sodium sulfate. The solvent was evaporated under reduced pressure, and the product was purified by column chromatography (200-300 mesh silica gel, ethyl acetate:petroleum ether:dichloromethane=1:30:1 to 1:6:1) to give (6-fluoro-2-ethylimidazo[1,2-a]pyridin-3-yl)-(4-methoxyphenyl)methanone (59) (390 mg). The yield was 19.5%.

Experimental procedures of Steps B, C and D were carried out according to the preparation methods of Steps C, D and E in Example 1 to give (3,5-dibromo-4-hydroxyphenyl)(2-ethyl-6-fluoro-5,6,7,8-tetrahydroimidazo[1,2-a]pyridin-3-yl) methanone (62). $^1$H NMR (DMSO-d$_6$, 400 MHz) δ 7.80 (s, 2H), 4.98-4.96 (m, 1H), 4.56-4.51 (m, 1H), 4.42-4.37 (m, 1H), 3.01 (t, J=6.4 Hz, 2H), 2.33-2.21 (m, 4H), 1.06 (t, J=7.2 Hz, 3H). MS (EI, m/z): 433.0 [M+H]$^+$.

Example 13

Synthesis of 3-bromo-5-((2-ethyl-5,6,7,8-tetrahydroimidazo[1,2-a]pyridin-3-yl)hydroxymethyl)-2-hydroxyl benzonitrile (63)

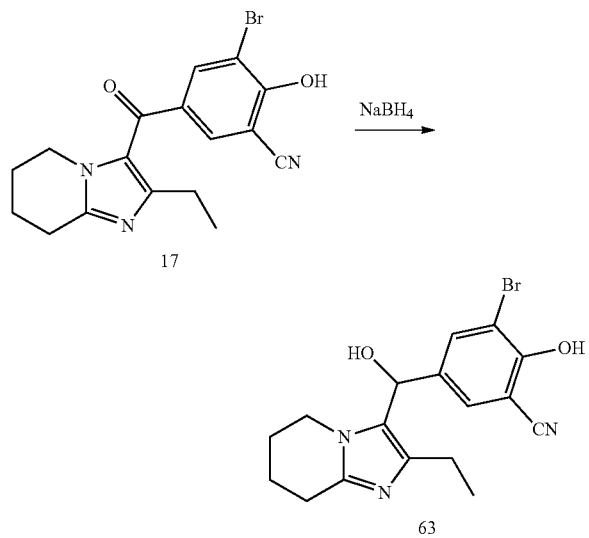

Sodium borohydride (90 mg, 2.4 mmol) was added to a solution of compound 17 (90 mg, 0.24 mmol) in anhydrous THF (7 mL), stirred at room temperature for 1 hour, and the pH value was adjusted to 5-6 with 2 M citric acid solution after adding water (10 mL). The mixture was extracted with ethyl acetate (15 mL×2) and dried over anhydrous sodium sulfate. The solvent was evaporated under reduced pressure and the product was purified by column chromatography (200-300 mesh silica gel, ethyl acetate:petroleum ether=1:2 to 5:1) to give 3-bromo-5-((2-ethyl)-5,6,7,8-tetrahydroimidazo[1,2-a]pyridin-3-yl)hydroxymethyl)-2-hydroxybenzonitrile (63) (8 mg). The yield was 8.89%. MS (EI, m/z): 376.10 [M+H]$^+$.

Example 14

Inhibition Assay of Uric Acid Transport for Compounds in HEK293-hURAT1 Transfection Cell Line I. Materials Zurampic was purchased from Chengdu Yichao Pharmaceutical Technology Co., Ltd. The plasmid pCMV6-hURAT1 was purchased from Origene Technologies, Inc. Geneticin (G418) was purchased from Sangon Biotech Co., Ltd. HEK293 cell line was purchased from the Cell Resource Center of Shanghai Institutes for Biological Sciences of the Chinese Academy of Sciences. Poly-lysine was purchased from Sigma-Aldrich Co. LLC. $^{14}$C-uric acid was purchased from American Radiolabeled Chemicals, Inc. Sodium gluconate, potassium gluconate, calcium gluconate, KH$_2$PO$_4$, MgSO$_4$, glucose and HEPES were purchased from Sinopharm Chemical Reagent Co., Ltd. DMEM culture medium and fetal bovine serum were purchased from Thermo Fisher Scientific Inc.

II. Experimental Methods and Results

1. Construction of a HEK293 stable cell line with high expression of hURAT1:

The plasmid pCMV6-hURAT1 was transfected into HEK293 cells, then the stable strain was obtained by the G418 (final concentration of 500 μg/mL) resistance screening, which is the high expression of hURAT1 transporter membrane protein. It can be used for in vitro inhibition assay of uric acid transporter hURAT1 (Weaver Y M, Ehresman D J, Butenhoff J L, et al. Roles of rat renal organic anion transporters in transporting perfluorinated carboxylates with different chain lengths. Toxicological Sciences, 2009, 113 (2):305-314).

2. Coating 24-well plate: to a coated 24-well plate was added 200 μl of 0.1 mg/mL poly-lysine per well and the plate was left overnight. Poly-lysine was removed from wells. The wells were cleaned thoroughly with steriled water and dried for use.

3. To the above coated 24-well plate was added HEK293-hURAT1 stable cells (2×10$^5$ cells per well). The cells were cultured at 37° C. under 5% CO$_2$ for 3 days.

4. Preparation of HBSS buffer: the following reagents were weighed according to the final concentration of 125 mM sodium gluconate, 4.8 mM potassium gluconate, 1.3 mM calcium gluconate, 1.2 mM KH$_2$PO$_4$, 1.2 mM MgSO$_4$, 5.6 mM glucose and 25 mM HEPES. Deionized water was added to reach the corresponding volume, and the solution was fully mixed to give HBSS (pH value: 7.4). The buffer was stored at −20° C. in a refrigerator.

5. At the day of experiment, the HBSS buffer was taken out of the refrigerator and warmed to 37° C. in a water bath. Taken out the 24-well plate with HEK293-hURAT1 stable cells, removed the culture medium and washed cells with HBSS, then add 160 μL of HBSS and 20 μL test compound per well. The final concentration of tested compound per well is 500 nM. The blank control well contains only 180 μL of HBSS without tested compound. The plate was placed at room temperature for 10 minutes.

6. To each well was added 20 μL of 50 μM $^{14}$C-uric acid. The 24-well plate was placed at room temperature for 20 minutes.

7. The solution in each well was removed and the cells in each well were washed with the pre-cooled HBSS buffer. To each well was added 0.2 M NaOH to dissolve the cells. The solution containing cell fragments was collected and the appropriate amount of scintillation liquid was added. The radioisotope intensity of the $^{14}$C-Uric acid (CPM value) was then detected by using PerkinElmer MicroBeta Trilux 1450 liquid scintillation analyzer.

8. In HEK293 transfected cell lines, the formula for calculating the inhabitation rate of uric acid transport for compounds was shown as below (Table 1), the CPM value of the tested compounds was represented by $CPM_{(tested\ compound)}$ and the CPM value of the blank control was represented by $CPM_{(blank\ control)}$. All tests were repeated three times, and the results were averaged and the standard deviation (SD) was calculated:

$$\text{Inhibition rate}(\%)_{(500\ nM\ compound\ concentration)} = (CPM_{(blank\ control)} - CPM_{(test\ compound)}) / CPM_{(blank\ control)} \times 100\%$$

III. Experimental Results

The results showed that in comparison with the control drug Zurampic at the concentration of 500 nM, the compounds of the invention (in particular, 5, 10, 17, 23, 25, 41, 42, 43 and 48) have very good inhibitory effects of uric acid transport in HEK293-hURAT1 transfection cell line.

TABLE 1

Inhibition rates of uric acid transport for test compounds and Zurampic in HEK293-hURAT1 transfection cell line

| Compound number or drug | Inhibition rate of uric acid transport, ±SD (%) (compound concentraton: 500 nM) |
|---|---|
| Zurampic | 27.59 ± 2.89 |
| 5 | 53.43 ± 4.54 |
| 10 | 47.53 ± 3.12 |
| 17 | 47.46 ± 0.14 |
| 23 | 47.54 ± 1.65 |
| 25 | 47.58 ± 4.12 |
| 32 | 43.39 ± 2.40 |
| 41 | 46.24 ± 6.18 |
| 42 | 47.65 ± 3.08 |
| 43 | 53.17 ± 9.36 |
| 48 | 46.11 ± 4.91 |
| 58 | 38.62 ± 6.30 |
| 63 | 42.32 ± 2.60 |

What is claimed is:

1. A compound, a (4-Hydroxyphenyl) (diazole) ketone derivative, as represented by the structure of formula (I-1) or pharmaceutically acceptable salts thereof

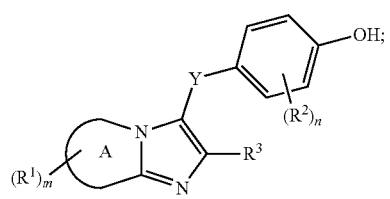
(I-1)

wherein,
A is a non-aromatic six-membered ring;
Y is carbonyl or;
$R^1$ is one or more selected from the group consisting of hydrogen, deuterium, hydroxy, halogen, nitro, amino, cyano, $C_{1-5}$ alkyl, substituted $C_{1-5}$ alkyl, substituted $C_{1-3}$ amino, $C_{1-3}$ alkoxy, substituted $C_{1-3}$ alkoxy and $C_{1-5}$ alkylthio;

$R^2$ is one or more selected from the group consisting of hydrogen, deuterium, hydroxy, halogen, nitro, amino, cyano, $C_{1-4}$ alkyl, substituted $C_{1-3}$ alkyl, $C_{2-3}$ alkenyl, $C_{2-3}$ alkynyl, substituted $C_{1-3}$ amino, $C_{1-5}$ alkoxy, substituted $C_{1-5}$ alkoxy and $C_{1-5}$ alkylthio;

$R^3$ is $C_{1-4}$ alkyl, substituted $C_{1-4}$ alkyl or $C_{3-4}$ cycloalkyl;

m is an integer from 0 to 3;

n is an integer from 1 to 3.

2. The compound or pharmaceutically acceptable salt thereof according to claim 1, wherein ring A is a cyclohexene ring or a non-aromatic six-membered ring; the non-aromatic six-membered ring containing at least one O or/and N atom.

3. The compound or pharmaceutically acceptable salt thereof according to claim 1, wherein $R^1$ is selected from one or more of the group consisting of hydrogen, deuterium, fluorine, chlorine, bromine, hydroxy, cyano, $C_{1-3}$ alkyl, $C_{1-3}$ haloalkyl and $C_{1-3}$ alkoxy; m is 0, 1 or 2.

4. The compound or pharmaceutically acceptable salt thereof according to claim 1, wherein $R^2$ is selected from one or more of the group consisting of hydrogen, deuterium, halogen, cyano, vinyl, ethynyl, $C_{1-2}$ alkyl, substituted $C_{1-2}$ alkyl, $C_{1-2}$ alkoxy, substituted $C_{1-2}$ alkoxy, $C_{1-2}$ alkylthio, and substituted $C_{1-2}$ alkylthio; n is 1 or 2.

5. The compound or pharmaceutically acceptable salt thereof according to claim 1, wherein $R^3$ is selected from the group consisting of methyl, ethyl, n-propyl, isopropyl, cyclopropyl and cyclobutyl.

6. The compound or pharmaceutically acceptable salt thereof according to claim 1, wherein the compound is selected from the following:

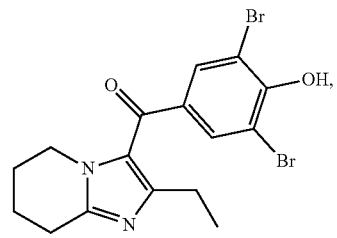

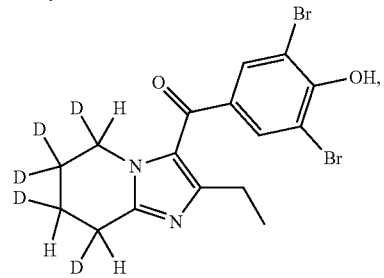

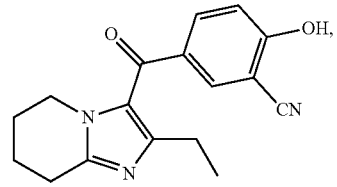

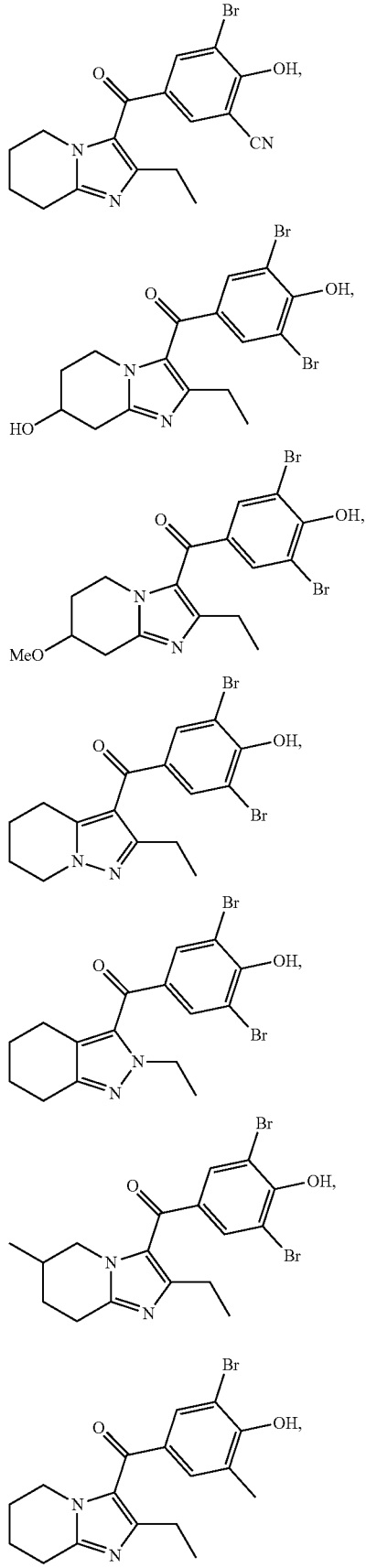
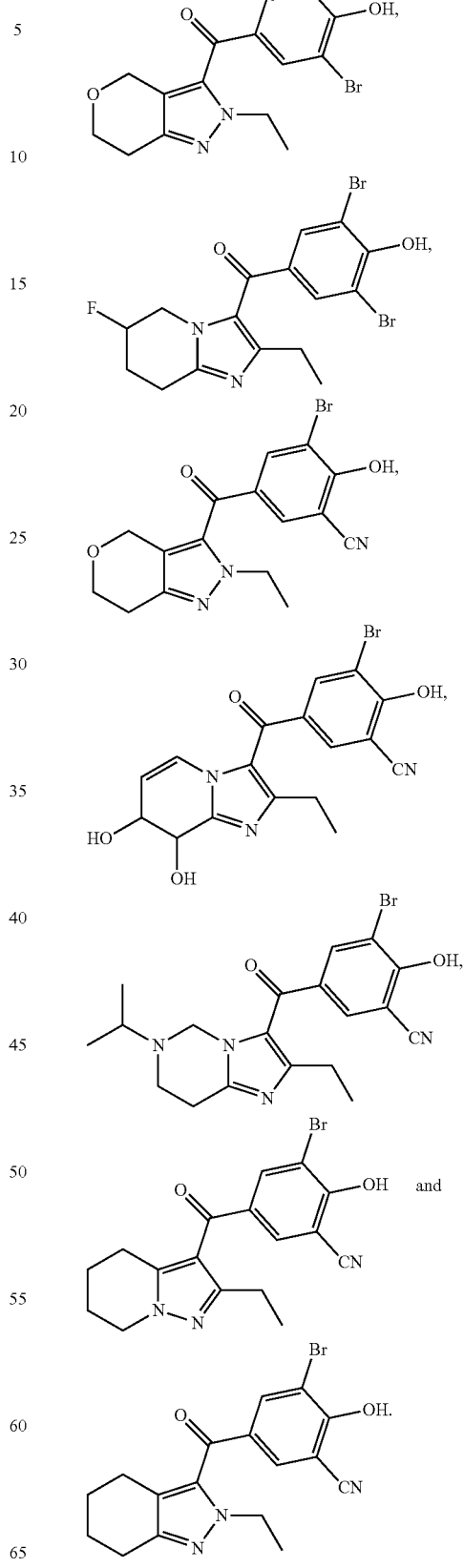

7. A pharmaceutical composition comprising the compound or pharmaceutically acceptable salt thereof according to claim 1 as an active ingredient and pharmaceutically acceptable excipients.

8. The compound or pharmaceutically acceptable salt thereof according to claim 1, wherein the compound or pharmaceutically acceptable salt thereof is prepared as a medicament for promoting uric acid excretion.

9. The compound or pharmaceutically acceptable salt thereof according to claim 1, wherein $R^1$, or $R^2$ is selected from the group consisting of hydroxy, halogen, nitro, amino and cyano.

10. The compound or pharmaceutically acceptable salt thereof according to claim 4, wherein $R^2$ is selected from the group consisting of deuterium, halogen, $C_{1-2}$ alkyl, and $C_{1-2}$ alkoxy.

* * * * *

UNITED STATES PATENT AND TRADEMARK OFFICE
CERTIFICATE OF CORRECTION

PATENT NO.        : 11,597,725 B2
APPLICATION NO.   : 16/617426
DATED             : March 7, 2023
INVENTOR(S)       : Dongfang Shi et al.

Page 1 of 1

It is certified that error appears in the above-identified patent and that said Letters Patent is hereby corrected as shown below:

On the Title Page

Applicant should be:
(71) Applicant: JIANGSU ATOM BIOSCIENCE AND PHARMACEUTICAL CO., LTD., Suzhou (CN)

Signed and Sealed this
Eleventh Day of April, 2023

Katherine Kelly Vidal
*Director of the United States Patent and Trademark Office*